US012653606B2

(12) United States Patent
Viswanathan

(10) Patent No.: US 12,653,606 B2
(45) Date of Patent: Jun. 16, 2026

(54) APPARATUS AND METHODS FOR TUMOR ABLATION

(71) Applicant: Alpfa Medical, Inc., Palo Alto, CA (US)

(72) Inventor: Raju Viswanathan, Palo Alto, CA (US)

(73) Assignee: Alpfa Medical, Inc., Palo Alto, CA (US)

( * ) Notice: Subject to any disclaimer, the term of this patent is extended or adjusted under 35 U.S.C. 154(b) by 0 days.

(21) Appl. No.: 18/964,044

(22) Filed: Nov. 29, 2024

(65) Prior Publication Data

US 2025/0090221 A1 Mar. 20, 2025

Related U.S. Application Data

(63) Continuation of application No. PCT/US2023/023902, filed on May 30, 2023.
(Continued)

(51) Int. Cl.
*A61B 18/14* (2006.01)
*A61B 18/00* (2006.01)

(52) U.S. Cl.
CPC .................... *A61B 18/1477* (2013.01); *A61B 2018/00077* (2013.01); *A61B 2018/00083* (2013.01);
(Continued)

(58) Field of Classification Search
CPC ...... A61B 2018/00577; A61B 18/1492; A61B 18/1206; A61B 18/1477;
(Continued)

(56) References Cited

U.S. PATENT DOCUMENTS 3,915,945 A    10/1975   Takahashi et al.
5,439,440 A *   8/1995   Hofmann ............... A61N 1/327
                                                    604/20
(Continued)

FOREIGN PATENT DOCUMENTS

CN       112641503 A     4/2021
EP         1613387 B1    1/2008
(Continued)

OTHER PUBLICATIONS

International Preliminary Report on Patentability for International Application No. PCT/US2023/023902 mailed Dec. 12, 2024, 17 pages.
(Continued)

*Primary Examiner* — Michael F Peffley
*Assistant Examiner* — Amanda L Zink
(74) *Attorney, Agent, or Firm* — COOLEY LLP

(57) ABSTRACT

Systems, devices, and methods described herein relate to catheter devices for therapy delivery in tumor treatment applications. In some embodiments, a catheter device includes a shaft defining a lumen, and a needle device disposed in the lumen, the needle device having a distal portion that includes an exposed electrical conductor, where the distal portion of the needle device is configured to be extended out of the lumen. The needle device can be configured to receive a pulsed voltage waveform and to deliver a pulsed electric field via the exposed electrical conductor to ablate surrounding tissue.

29 Claims, 30 Drawing Sheets

Related U.S. Application Data

(60) Provisional application No. 63/348,215, filed on Jun. 2, 2022.

(52) U.S. Cl.
CPC ............... *A61B 2018/00482* (2013.01); *A61B 2018/00577* (2013.01); *A61B 2018/00613* (2013.01)

(58) Field of Classification Search
CPC .... A61B 2018/1467; A61B 2018/0016; A61B 2018/00702; A61B 18/14; A61B 2018/143; A61B 18/148; A61B 2018/00083; A61B 18/1485; A61B 2018/1425; A61B 18/1482; A61B 2018/1475; A61B 2018/1861; A61B 2018/00613
See application file for complete search history.

(56) References Cited

U.S. PATENT DOCUMENTS

| | | | |
|---|---|---|---|
| 5,476,495 A | 12/1995 | Kordis et al. | |
| 5,494,042 A | 2/1996 | Panescu et al. | |
| 5,702,359 A * | 12/1997 | Hofmann | A61N 1/327 |
| | | | 607/148 |
| 5,904,680 A | 5/1999 | Kordis et al. | |
| 6,086,532 A | 7/2000 | Panescu et al. | |
| 7,070,596 B1 | 7/2006 | Woloszko et al. | |
| 8,048,067 B2 | 11/2011 | Davalos et al. | |
| 8,504,147 B2 | 8/2013 | Deem et al. | |
| 8,870,863 B2 | 10/2014 | Leung et al. | |
| 9,101,375 B2 * | 8/2015 | Biadillah | A61B 34/76 |
| 9,233,241 B2 * | 1/2016 | Long | A61B 18/1492 |
| 9,387,031 B2 | 7/2016 | Stewart et al. | |
| 9,427,284 B2 | 8/2016 | Moss et al. | |
| 10,136,942 B1 | 11/2018 | Cosman, Jr. et al. | |
| 10,722,288 B2 | 7/2020 | Wu et al. | |
| 10,842,572 B1 | 11/2020 | Viswanathan | |
| 10,893,905 B2 | 1/2021 | Viswanathan et al. | |
| 11,633,230 B2 | 4/2023 | Stewart et al. | |
| 11,974,804 B2 | 5/2024 | Zarins et al. | |
| 12,076,072 B2 | 9/2024 | Athos et al. | |
| 12,114,919 B2 | 10/2024 | Forsyth et al. | |
| 12,150,698 B2 | 11/2024 | Viswanathan et al. | |
| 12,239,364 B2 | 3/2025 | Govari et al. | |
| 12,521,174 B2 | 1/2026 | Viswanathan | |
| 12,558,157 B2 | 2/2026 | Viswanathan et al. | |
| 2001/0012934 A1 | 8/2001 | Chandrasekaran et al. | |
| 2002/0087208 A1 | 7/2002 | Koblish et al. | |
| 2003/0178032 A1 * | 9/2003 | Ingle | A61B 18/1485 |
| | | | 606/41 |
| 2004/0204669 A1 * | 10/2004 | Hofmann | A61N 1/30 |
| | | | 604/21 |
| 2008/0287857 A1 * | 11/2008 | Kjeken | A61N 1/327 |
| | | | 604/21 |
| 2009/0062788 A1 * | 3/2009 | Long | A61B 18/14 |
| | | | 606/41 |
| 2011/0087211 A1 | 4/2011 | Kulesa et al. | |
| 2012/0157993 A1 | 6/2012 | Jenson et al. | |
| 2012/0265198 A1 | 10/2012 | Crow et al. | |
| 2013/0030430 A1 | 1/2013 | Stewart et al. | |
| 2013/0310823 A1 * | 11/2013 | Gelfand | A61M 25/0082 |
| | | | 606/41 |
| 2014/0276764 A1 | 9/2014 | Shuman et al. | |
| 2015/0272662 A1 | 10/2015 | Shuman et al. | |
| 2015/0289929 A1 | 10/2015 | Toth et al. | |
| 2016/0113709 A1 | 4/2016 | Maor | |
| 2017/0065339 A1 | 3/2017 | Mickelsen | |
| 2018/0117287 A1 | 5/2018 | Krautkremer et al. | |
| 2018/0153467 A1 * | 6/2018 | Lichtenstein | A61N 1/0551 |
| 2018/0303543 A1 * | 10/2018 | Stewart | A61B 18/1492 |
| 2019/0069950 A1 | 3/2019 | Viswanathan et al. | |
| 2019/0298442 A1 | 10/2019 | Ogata et al. | |

| | | | |
|---|---|---|---|
| 2020/0129230 A1 | 4/2020 | Forsyth et al. | |
| 2020/0205892 A1 | 7/2020 | Viswanathan et al. | |
| 2021/0085387 A1 | 3/2021 | Amit et al. | |
| 2021/0161582 A1 | 6/2021 | Byrd et al. | |
| 2021/0212760 A1 | 7/2021 | Perfler | |
| 2022/0054188 A1 | 2/2022 | Palushi et al. | |
| 2022/0104875 A1 | 4/2022 | Gleiman et al. | |
| 2022/0133397 A1 | 5/2022 | Morris et al. | |
| 2022/0296295 A1 | 9/2022 | Howard et al. | |
| 2023/0054269 A1 | 2/2023 | Govari et al. | |
| 2023/0068059 A1 | 3/2023 | Turovskiy et al. | |
| 2023/0149070 A1 | 5/2023 | Olson et al. | |
| 2023/0165629 A1 | 6/2023 | Tehrani et al. | |
| 2023/0218340 A1 | 7/2023 | Werneth et al. | |
| 2024/0099769 A1 | 3/2024 | Sharma | |
| 2024/0180613 A1 | 6/2024 | D'Agostino et al. | |
| 2024/0216052 A1 | 7/2024 | Rodriguez Soto et al. | |
| 2025/0000574 A1 | 1/2025 | Bar-Tal et al. | |
| 2025/0009404 A1 | 1/2025 | Sabban et al. | |
| 2025/0056709 A1 * | 2/2025 | Rivaud | H05K 1/0271 |
| 2025/0073354 A1 * | 3/2025 | Nedergaard | A61K 48/0033 |
| 2025/0082396 A1 | 3/2025 | Bar-Tal et al. | |
| 2025/0120764 A1 | 4/2025 | Viswanathan | |
| 2025/0221761 A1 * | 7/2025 | Viswanathan | A61B 18/1482 |
| 2025/0246316 A1 | 7/2025 | Villongco et al. | |
| 2025/0281231 A1 | 9/2025 | DeSimone et al. | |
| 2025/0352258 A1 | 11/2025 | O'Brien et al. | |
| 2026/0033881 A1 | 2/2026 | Viswanathan | |

FOREIGN PATENT DOCUMENTS

| | | |
|---|---|---|
| WO | WO-2011056464 A2 | 5/2011 |
| WO | WO-2016060983 A1 | 4/2016 |
| WO | WO-2016090175 A1 | 6/2016 |
| WO | WO-2019055512 A1 | 3/2019 |
| WO | WO 2021043779 | 3/2021 |
| WO | WO-2021119479 A1 | 6/2021 |
| WO | WO-2021195311 A1 | 9/2021 |
| WO | WO-2022058865 A1 | 3/2022 |
| WO | WO-2022192522 A1 | 9/2022 |
| WO | WO-2023220419 A1 | 11/2023 |
| WO | WO-2023235337 A1 | 12/2023 |
| WO | WO-2023250370 A1 | 12/2023 |
| WO | WO-2024041285 A1 | 2/2024 |
| WO | WO 2024047215 | 3/2024 |
| WO | WO-2024073765 A2 | 4/2024 |
| WO | WO-2024092134 A1 | 5/2024 |
| WO | WO-2024157117 A1 | 8/2024 |
| WO | WO-2025137674 A1 | 6/2025 |
| WO | WO-2025213017 A1 | 10/2025 |

OTHER PUBLICATIONS

International Search Report and Written Opinion for PCT Application No. PCT/US2023/023902 dated Sep. 20, 2023, 25 pages.

European Application No. 22193699.0, titled "An Electroporation Probe and Apparatus," filed Sep. 2, 2022; Applicant: Mirai Medical Limited, 30 pages.

EP Application No. 23801187.8, Office Action mailed Mar. 19, 2026; Applicant Alpfa Medical, Inc.; 11 total pages.

U.S. Appl. No. 19/354,755, Non-Final Office Action mailed Feb. 24, 2026; Inventor Viswanathan, Raju et al.; 30 pages.

International Application No. PCT/US2023/068807, International Preliminary Report on Patentability mailed Jan. 2, 2025; Applicant Alpfa Medical, Inc.; 12 pages.

International Application No. PCT/US2023/068807, International Search Report and Written Opinion dated Oct. 11, 2023; Applicant Alpfa Medical, Inc.; 20 pages.

International Application No. PCT/US2023/075681, International Search Report and Written Opinion dated Apr. 3, 2024; Applicant Alpfa Medical, Inc.; 16 pages.

International Application No. PCT/US2024/061649, International Search Report and Written Opinion mailed May 20, 2025; Applicant Alpfa Medical, Inc.; 19 pages.

International Application No. PCT/US2025/023151, International Search Report and Written Opinion mailed Jul. 11, 2025; Applicant Alpfa Medical, Inc.; 14 pages.

(56) References Cited

OTHER PUBLICATIONS

International Application No. PCT/US2023/075681, Invitation to Pay Additional Fees and Partial Search Report dated Feb. 8, 2024; Applicant Alpfa Medical, Inc.; 11 pages.
International Application No. PCT/US2024/061649, Invitation to Pay Additional Fees mailed Mar. 27, 2025; Applicant Alpfa Medical, Inc.; 15 pages.
U.S. Appl. No. 18/999,981, Office Action mailed Apr. 15, 2025; Inventor Viswanathan, Raju; 14 pages.
U.S. Appl. No. 19/094,761, Office Action mailed May 19, 2025; Inventor Viswanathan, Raju; 8 pages.
U.S. Appl. No. 18/999,981, Office Action mailed Aug. 6, 2025; Inventor Viswanathan, Raju; 11 pages.

* cited by examiner

1

APPARATUS AND METHODS FOR TUMOR ABLATION

CROSS-REFERENCE TO RELATED APPLICATIONS

This application is a continuation of PCT Application No. PCT/US2023/023902, filed May 30, 2023, and titled "APPARATUS AND METHODS FOR TUMOR ABLATION," which claims priority to and the benefit of U.S. Provisional Patent Application No. 63/348,215, filed Jun. 2, 2022, titled "APPARATUS AND METHODS FOR TUMOR ABLATION," the disclosure of each of which is incorporated by reference in its entirety.

BACKGROUND

The development of tools and methods for therapy delivery for the treatment of tumors or various forms of cancer in soft tissue continues to remain a subject of much interest. While in many cases, various options for tumor treatment are available, there is a continuing search for the delivery of effective treatment that minimizes or eliminates collateral tissue damage and side effects.

Irreversible electroporation, also known as pulsed field ablation, has been previously explored in the context of surgical treatment of tumors. In surgical applications, the quest for an optimal toolset is ongoing. In the context of minimally invasive approaches, much remains to be done to develop effective minimally invasive tools that are usable while at the same time ensuring localized treatment that minimizes collateral damage.

The present disclosure addresses the need for minimally invasive devices for the efficient and effective delivery of pulsed field ablation therapy, especially for tumor treatment such as, for example, the treatment of pancreatic cancer or lung tumors. Pulsed field ablation procedures can be rapid while at the same time minimizing collateral tissue damage often seen in thermal-based therapies. At the same time, post-procedural healing can be relatively quick with minimal side-effects.

SUMMARY

The present disclosure discloses tools and devices for minimally invasive access to internal organs for therapy delivery in tumor treatment applications. Specifically, the devices of the present disclosure can have one or more lumens for the passage of a needle or tissue-puncturing device. In some embodiments, the needle can take the form of a wire or wire-like device. In embodiments, the distal end of the lumen of the device can have a wedge-like portion on one side that reduces the effective inner diameter of the lumen and constrains the orientation at which the needle or wire emerges from the device lumen. In embodiments, the wedge-like portion can be curvilinear in shape. This wedge-like portion can serve as a local support for the wire as it emerges from the lumen at an orientation that is generally different from the orientation of the long axis of the lumen. In the case of a multi-lumen device with between about 2 and about 8 distinct lumens, each needle can emerge from its respective lumen at a different orientation relative to each other and relative to the orientation of the long axis of the device.

In embodiments, the distal end of the shaft of the lumen can be angled away from the long axis of the device on one side so as to present an angled exit for the needle. In some embodiments, the angled portion can have a straight edge, while in other embodiments, it can have a curved edge. In embodiments, the device can have a multiplicity of such lumens, with the distal end of the shaft of each lumen angled away from the long axis of the device, such that each needle can emerge from a respective lumen at a different orientation relative to the other needles of the device and relative to the orientation of the long axis of the device.

In embodiments, the device can be a catheter device with one or more lumens that is itself passed through a working channel or instrumentation channel of an endoscope device, with the endoscope device being able to acquire an image of the catheter device with an imaging modality such as, for example, optical imaging or ultrasound imaging. The endoscopic imaging modality can be used to guide the placement of the catheter device at a tissue surface and to visualize the passage of one or more needles as they emerge from the catheter device and puncture the tissue surface or enter an adjacent anatomical organ. For example, the catheter device can be placed via an endoscope in the stomach or duodenum, and needles can be inserted from the catheter device into the duodenal wall so as to enter the pancreas for subsequent therapy delivery. In embodiments, the catheter device can be inserted alongside an endoscopic device, with the endoscopic device then used to image and guide the placement of the catheter device at a tissue surface and to visualize needle insertion. The catheter device can be deflectable in some embodiments, so that the orientation of the distal end can be adjusted for suitable tissue apposition.

In embodiments, a substantial portion of the length of the wire can be insulated with one or more layers of insulation capable of withstanding a voltage of at least about 500V across its thickness without dielectric breakdown. In embodiments, the insulation can be in the form of a coating such as a parylene coating, while in others, the insulation can comprise polymeric material in tubular form. In embodiments, the distal end of the wire can comprise a fine, sharp tip for easy puncturing of tissue. In embodiments, a portion of the wire proximal to the distal portion can have a slight bend in its free or unstressed state.

In embodiments, the distal portion of the wire can be helical in shape. The helix or helical portion is attached to the main body of the wire in coaxial fashion, i.e., the axis of winding of the helix coincides with the tangent to the wire just proximal to the helix. In this manner, twisting the wire (about its longitudinal axis) along with advancement produces a screw-like motion of the helix. When the distal portion of the wire is within the lumen of the device, the helix is naturally stretched compared to when the wire is in its unstressed state so that the helical shape of the wire can have a pitch or length between successive turns of the helix when in the lumen of the device that is larger than in its free or unstressed state. At the same time, the winding diameter of the helix is smaller when in the lumen of the device than in the unstressed state, e.g., for accommodation in the lumen of the device.

In use, the device with the helical needle is positioned just proximal to a tissue or organ surface that it is desired to penetrate with the needle. The proximal handle of the device includes a mechanism for screw-like advancement of the wire, e.g., so that the user turns a wheel, knob or other control mechanism to simultaneously rotate and advance the wire or needle. In one embodiment, the pitch of the advancement mechanism coincides with the pitch of the helix in its unstressed state. The proximal portion of the wire is held in an advancement mechanism in the handle which functions like a screw of given pitch. In embodiments, a single control mechanism can selectively engage any one of a multiplicity of needles via a selective mechanism, for example a slider. To advance the wire, the user rotates the knob or other control mechanism whereby the wire is rotated and advanced at the same time. This screw motion naturally advances the wire and as it emerges from the distal portion of the device, where the emerging portion of the needle or wire assumes its unstressed helical shape. Such rotation and advancement induces a corkscrew motion at the distal portion of the needle. At the tissue surface, the corkscrew motion of the distal portion of the needle serves to puncture and then advance the needle into the tissue; the winding diameter of the helical portion of the needle that is inserted into the tissue is now the unstressed, larger diameter. This provides for having a larger effective diameter of the inserted helical needle as compared to the winding diameter or helical diameter inside the device shaft. The larger effective diameter can help with generation of a suitable electric field for pulsed field ablation delivery.

In various embodiments, multiple lumens of the device can carry a multiplicity of needles in the form of various combinations of straight needles or helical needle wires. In embodiments, the device can have a central lumen surrounded by a set of outer lumens, while in other embodiments, there may only be outer lumens with no central lumen, with each lumen carrying a needle wire in the form of either a straight needle or a helical needle.

In embodiments, the catheter device, or its main shaft, can itself be a needle for percutaneous insertion. In such embodiments, a significant portion of the hollow metallic needle shaft can be coated with an insulation layer, e.g., such as parylene, with only the distal portion of the needle electrically exposed. The shaft of the device can contain one or more lumens that also function as electrical insulators, and smaller diameter outer needles can be passed through each such lumen. The smaller needles may also be coated with an insulation layer, e.g., such as parylene, along a significant portion of their lengths. The smaller needles emerge through openings in the distal portion of the main needle shaft that are proximal to the distal tip of the main needle shaft. The distal needle tip of the main needle shaft is sharpened in a shape that enables puncturing tissue for insertion. In use, the main needle is positioned at an appropriate puncture site for percutaneous insertion, for example, a thoracic site for treatment of a lung tumor. A puncture is made and the main needle is inserted under visual guidance, for example, through a modality such as computed tomography (CT) imaging. The main needle is advanced to a region of interest such as a tumor. Once the main needle is within the tumor, the outer needles are advanced through the openings in the distal shaft of the main needle.

The main needle and/or a subset of the outer needles can then be used for therapy delivery of a pulsed field ablation waveform, either in unipolar mode (e.g., all needles with one electrical polarity, and a reference patch placed on the subject with the opposite electrical polarity) or in bipolar mode (e.g., two different subsets of needles with opposite electrical polarities).

The needles or wires in any of the embodiments herein are generally metallic; for example, they can comprise a metallic alloy such as Nitinol or stainless steel. The needles can be attached or connected to an electrical conductor that attaches to a cable or connector cable for delivery of electrical energy from an appropriate generator that can deliver high voltage pulsed field ablation waveforms. Generally, such energy delivery is performed in either unipolar or bipolar mode. In unipolar mode, a subset of the needles has one electrical polarity, while a reference patch placed on the subject has the opposite electrical polarity. In bipolar mode, two different subsets of needles are energized with opposite electrical polarities. In embodiments, multiple paired subsets of needles can be energized in sequential fashion for energy delivery. The pulsed field ablation waveform can be either monophasic (e.g., every pulse delivered to an electrode pair has the same polarity) or biphasic in structure (e.g., consecutive pulses delivered to an electrode pair have opposite polarities). When the pulsed field ablation waveform is applied, the spatial distribution of the resulting electric field determines the zone of cell death. Depending on the value of the irreversible electroporation field strength threshold for a given targeted cell type, cells in a spatial zone where the electric field magnitude is greater than the threshold value are killed or ablated, while cells in other spatial zones where the electric field magnitude is below the threshold value survive.

In some embodiments, the catheter devices of the present disclosure can have an outer diameter in the approximate range of about 0.5 mm to about 5 mm, inclusive of all values and sub-ranges therebetween. In some embodiments, the needles or wires can have a diameter in the approximate range of about 0.15 mm to about 1.6 mm depending on the embodiment, inclusive of all values and sub-ranges therebetween. In the case of a helical needle, the pitch of the helix can be in the approximate range of between about 0.1 mm and about 4 mm, inclusive of all values and sub-ranges therebetween, and the diameter of the helix (measured on the winding diameter of the centerline) can be in the approximate range of between about 0.3 mm and about 4 mm, inclusive of all values and sub-ranges therebetween.

In some embodiments, an apparatus includes: a shaft defining a lumen; and a needle device disposed in the lumen, the needle device having a distal portion that includes an exposed electrical conductor, the distal portion of the needle device being configured to be extended out of the lumen at a non-zero angle with respect to a longitudinal axis of the shaft, the needle device being configured to receive a pulsed voltage waveform and to deliver a pulsed electric field via the exposed electrical conductor to ablate surrounding tissue.

In some embodiments, an apparatus includes: a shaft defining a set of one or more lumens; and first and second needle devices disposed in the set of lumens, each of the first and second needle devices having a distal portion that includes an exposed electrical conductor, the distal portions of the first and second needle devices configured to be extended out of the set of lumens at non-zero angles with respect to a longitudinal axis of the shaft, the first and second needle devices being configured to receive a pulsed voltage waveform and to collectively delivery a pulsed electric field via their respective exposed electrical conductors to ablate surrounding tissue.

In some embodiments, an apparatus includes: a shaft defining a lumen; and a needle device disposed in the lumen, the needle device having a distal portion that includes an exposed electrical conductor, the distal portion of the needle device having a helical geometry, the needle device being configured to receive a pulsed voltage waveform and to deliver a pulsed electric field via the exposed electrical conductor to ablate surrounding tissue.

In some embodiments, an apparatus includes: a shaft defining a lumen; and a needle device disposed in the lumen, the needle device having a distal portion that includes an exposed electrical conductor and a proximal portion that is electrically insulated with insulation configured to withstand a voltage of at least about 500 Volts without dielectric breakdown, the distal portion of the needle device having a substantially straight geometry, the needle device being configured to receive a pulsed voltage waveform and to deliver a pulsed electric field via the exposed electrical conductor to ablate surrounding tissue.

In some embodiments, an apparatus includes: a shaft defining a lumen; a needle device disposed in the lumen, the needle device having a distal portion that includes an exposed electrical conductor and a proximal portion that is electrically insulated with insulation configured to withstand a voltage of at least about 500 Volts without dielectric breakdown, the distal portion of the needle device having a helical geometry and configured to be extended outside of the lumen, the helical geometry having a diameter that is larger when the distal portion is extended outside of the lumen than when the distal portion is inside of the lumen, the needle device being configured to receive a pulsed voltage waveform and to deliver a pulsed electric field via the exposed electrical conductor to ablate surrounding tissue; and a proximal actuation assembly attached to proximal portions of the shaft and the needle device, the proximal actuation assembly configured to control a relative movement of the needle device relative to the catheter device.

In some embodiments, a method includes: extending a distal portion of a needle device outside of a lumen of a shaft of a catheter device positioned at an anatomical region of interest, the distal portion of the needle device including an exposed electrical conductor; puncturing, in response to extending the distal portion of the needle device outside of the lumen, a tissue of interest; moving the distal portion of the needle device within the tissue of interest to position a distal tip of the needle device at a target location; and applying voltage pulses to the needle device to deliver pulsed field ablation therapy.

In some embodiments, a method includes: extending distal portions of first and second needle devices outside of one or more lumens of a shaft of a catheter device positioned at an anatomical region of interest, the distal portions of the first and second needle devices including exposed electrical conductors; puncturing, in response to extending the distal portions of the first and second needle devices outside of the one or more lumens, a tissue of interest; moving the distal portions of the first and second needle devices within the tissue of interest to position distal tips of the first and second needle devices at target locations; and applying voltage pulses to the first and second needle devices to deliver pulsed field ablation therapy.

DETAILED DESCRIPTION

The device embodiments of the present disclosure generally provide means of deploying devices within soft tissue structures such as tumors for delivery of irreversible electroporation therapy. In some embodiments, the devices are intended for minimally invasive use (for instance, with or alongside an endoscope) and may be flexible or deflectable devices, while in other embodiments, they can be relatively rigid devices intended for percutaneous use.

Figure 1:
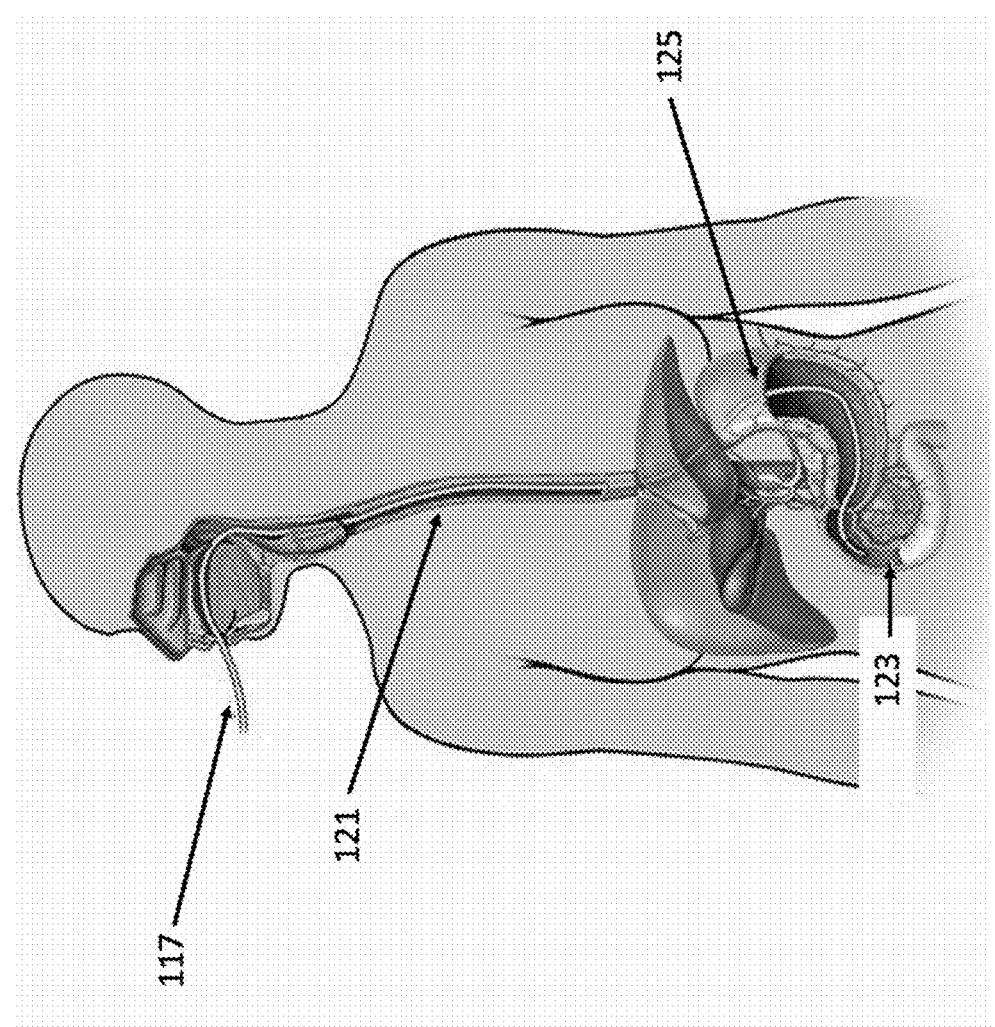
FIG. 1 is a schematic illustration of an endoscope passing through the stomach of a subject and placed in the duodenum.
Figure 2:
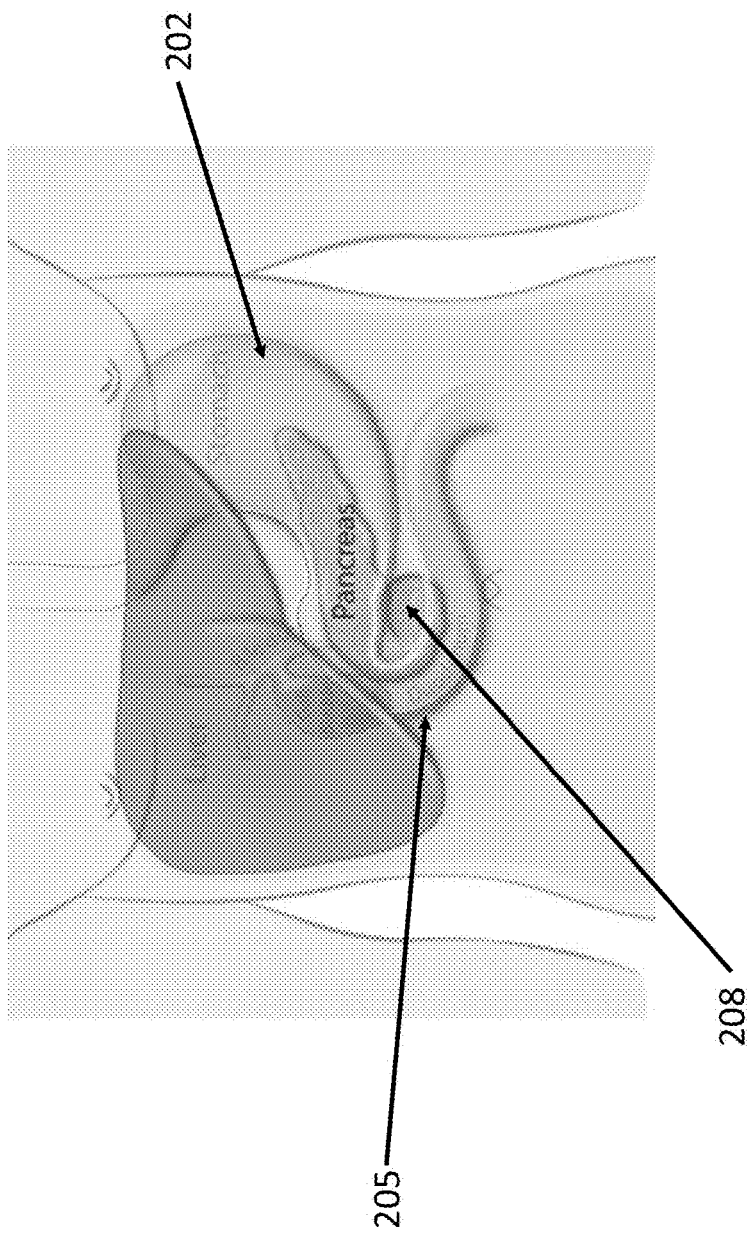
FIG. 2 provides an illustration of abdominal anatomy.

For the treatment of pancreatic tumors, endoscopic access can be gained to the stomach or the duodenum, and an adjacent organ such as the pancreas can be subsequently accessed by suitable puncture. FIG. 1 shows an endoscope 117 inserted through a subject's mouth and down the esophagus 121 to be positioned at the duodenum 123 after passing through the stomach 125. This type of positioning can place the endoscope near the pancreas. FIG. 2 illustrates the pancreas 208 relative to the stomach 202 and duodenum 205 within the abdominal anatomy.

Figure 3:
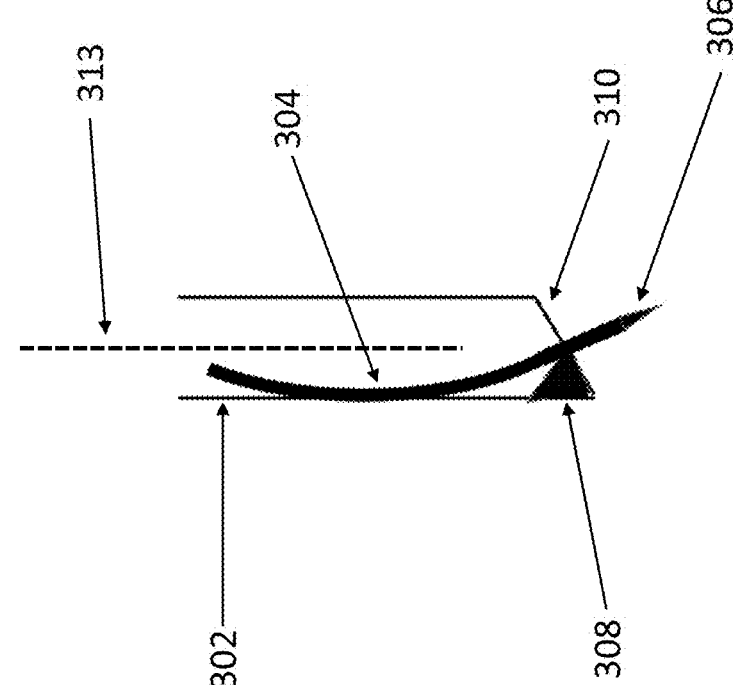
FIG. 3 is a schematic illustration of a single-lumen catheter or needle device with a wedged distal lumen, together with a needle, according to embodiments.

FIG. 3 is a schematic illustration of the distal portion of a single-lumen catheter 302 or needle device with a wedged distal lumen, together with a needle, according to embodiments. The distal end of the lumen has a wedge or wedge-like internal structure 308 that narrows the distal lumen, forcing the needle wire 304 as it is pushed out to extend from the distal opening 310 at an orientation that is angled away from the catheter long axis 313. In embodiments, the tip 306 of the wire 304 is shaped to a fine, sharp tip for tissue puncturing.

Figure 4:
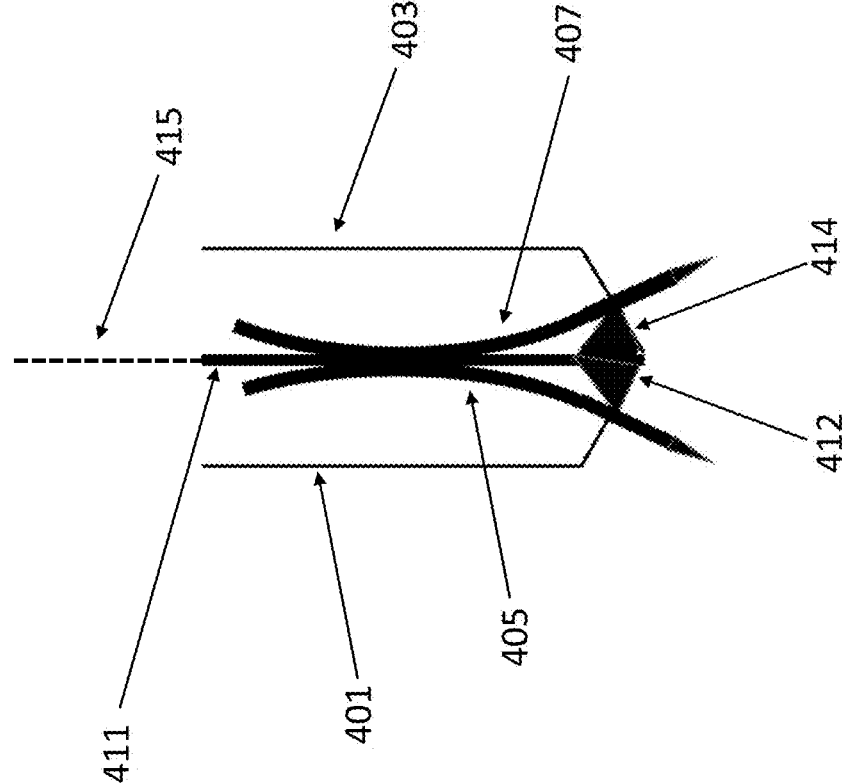
FIG. 4 is a schematic illustration of a dual-lumen catheter or needle device with two needles, according to embodiments.

In embodiments, the catheter device of the present disclosure can have multiple lumens. FIG. 4 illustrates a catheter device with two lumens 401 and 403 respectively carrying needles 405 and 407, according to embodiments. In embodiments, the lumen walls can be thicker in the portion 411 where they abut each other. Lumens 401 and 403 each have a wedged distal portion 412 and 414, respectively, that narrows the respective distal lumen, so that needle wires 405 and 407 emerge from the distal ends angled away from the long axis 415 of the device, and are also angled relative to each other.

Figure 5:
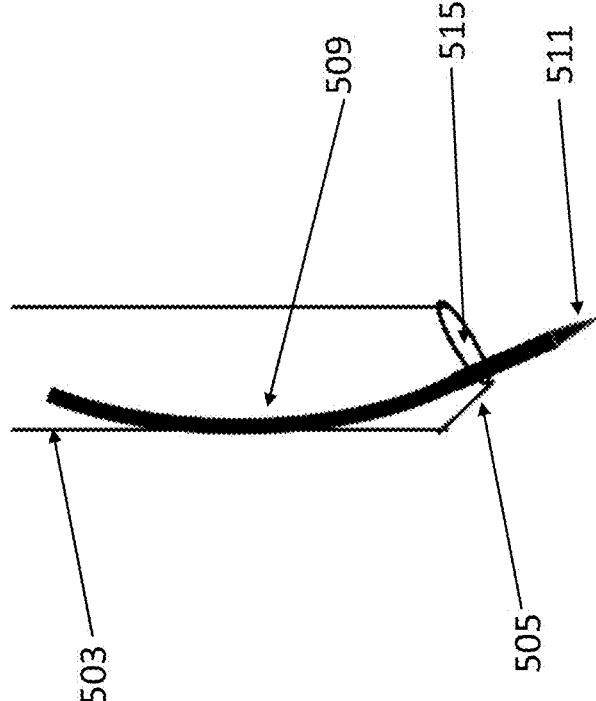
FIG. 5 is a schematic illustration of a single-lumen catheter or needle device with an angled nozzle-like distal portion, together with a needle, according to embodiments.

In embodiments, a lumen of a catheter device can have a distal end portion that is angled away from the long axis of the device on at least one side. FIG. 5 is a schematic illustration of a single-lumen catheter or device 503 with an angled nozzle-like distal portion 505 on one side of the shaft, carrying a needle wire 509 that extends out from the distal end 515 of the device with a needle tip 511 that is shaped to be sharp for tissue puncture, according to embodiments.

Figure 6:
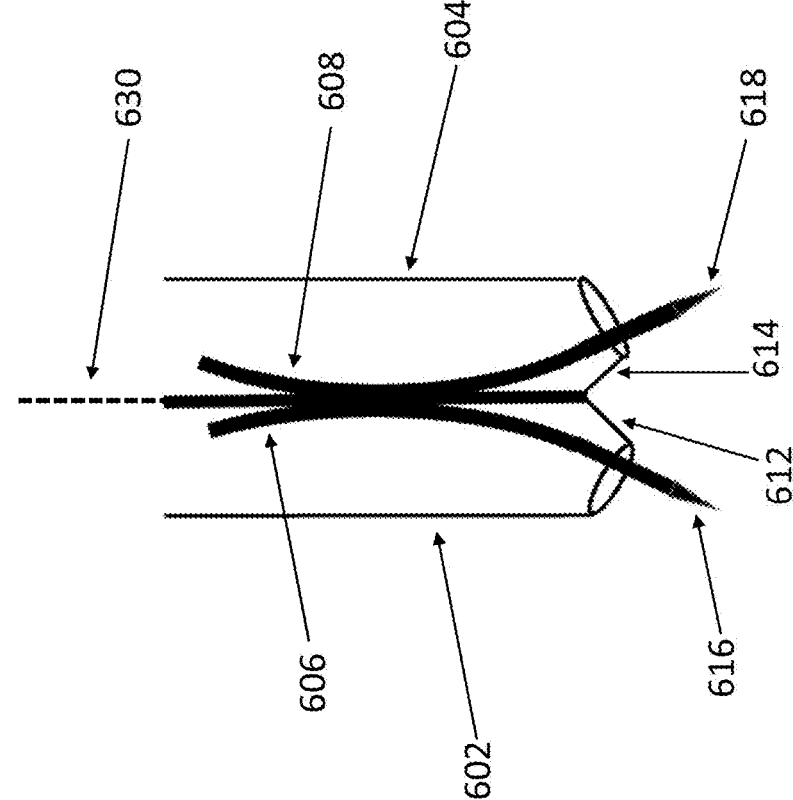
FIG. 6 illustrates a dual-lumen catheter device with each lumen having an angled nozzle-like distal portion, each lumen having a needle, according to embodiments.

In embodiments, the catheter device can have two or more lumens with distal end portions that are angled away from the long axis of the device on at least one side. FIG. 6 illustrates a dual-lumen catheter device with each lumen 602 and 604 having respective angled nozzle-like distal portions 612 and 614, each respective lumen carrying a needle 606 and 608, according to embodiments. As shown in FIG. 6, the distal ends 616 and 618 of respective needles 606 and 608 are angled away from the long axis 630 of the device, and are also angled away from each other.

Figure 7A:
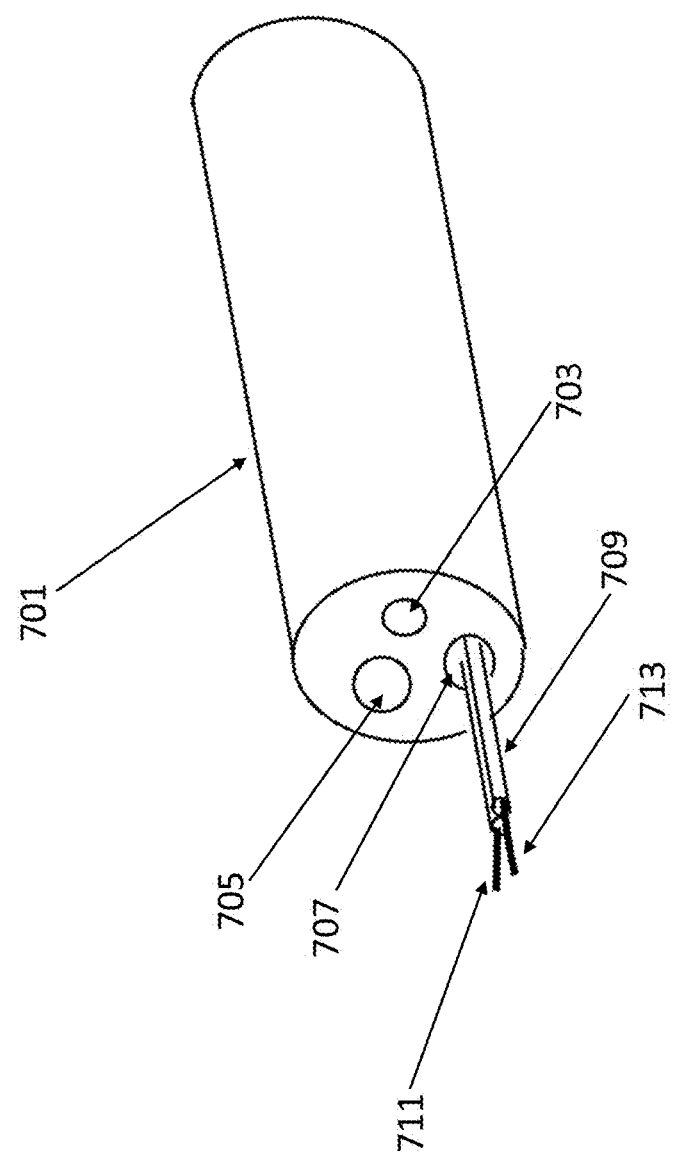
FIG. 7A is a sketch of the distal portion of an endoscope with multiple lumens, one of the lumens being used for the passage of a catheter device of the present invention, according to embodiments.
Figure 7B:
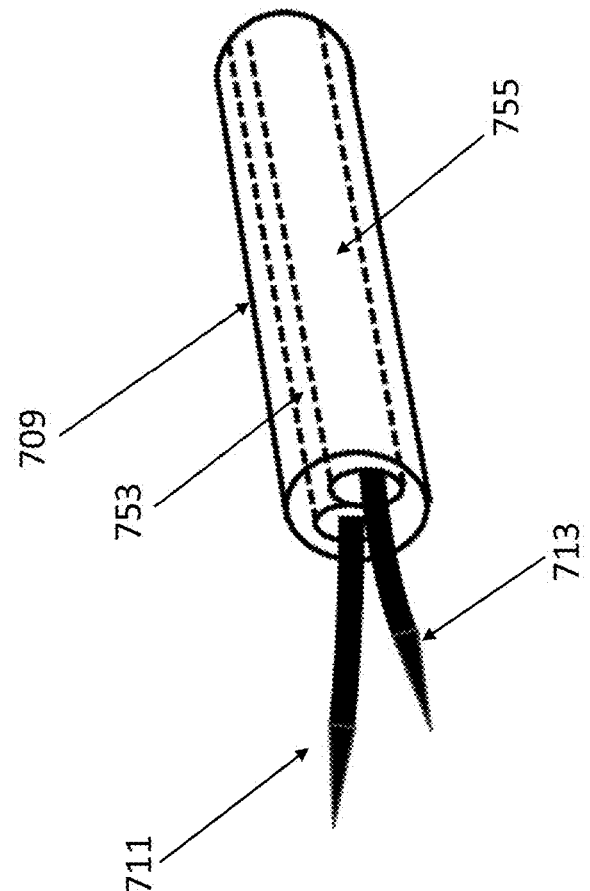
FIG. 7B is an illustration of a catheter device with an outer shaft and two inner lumens, each lumen carrying a needle, according to embodiments.

In embodiments, the catheter device of the present disclosure can itself be passed through a channel of an endoscope. FIG. 7A shows, for illustrative and example purposes, the distal portion of an endoscope 701 with multiple lumens 703, 705 and 707. The lumens 703 and/or 705 can be used for passage of an optical imaging fiber or camera or an ultrasound imaging catheter. The lumen or channel 707 is shown as being used for the passage of a catheter device 709 of the present disclosure. The catheter device 709 itself has two lumens carrying the needle wires 711 and 713. FIG. 7B depicts the distal portion of the catheter device 709 with lumens 753 and 755 respectively carrying needle wires 711 and 713. In use, the endoscope 701 is passed through the mouth and esophagus to the stomach and/or duodenum and placed adjacent to or near a tissue wall, for example, close to the pancreas. The catheter 709 is extended under image guidance from optical or ultrasound imaging carried out with the appropriate imaging device used with the endoscope and is positioned at an appropriate location for access to a suitable pancreatic site. The needles 711 and 713 are extended out of the catheter device 709 and used to puncture the stomach wall and enter the pancreas to access a target tumor site. Once the needles are positioned suitably in the pancreas, pulsed field ablation is delivered through the needles from a generator that is connected to the catheter.

Figure 8:
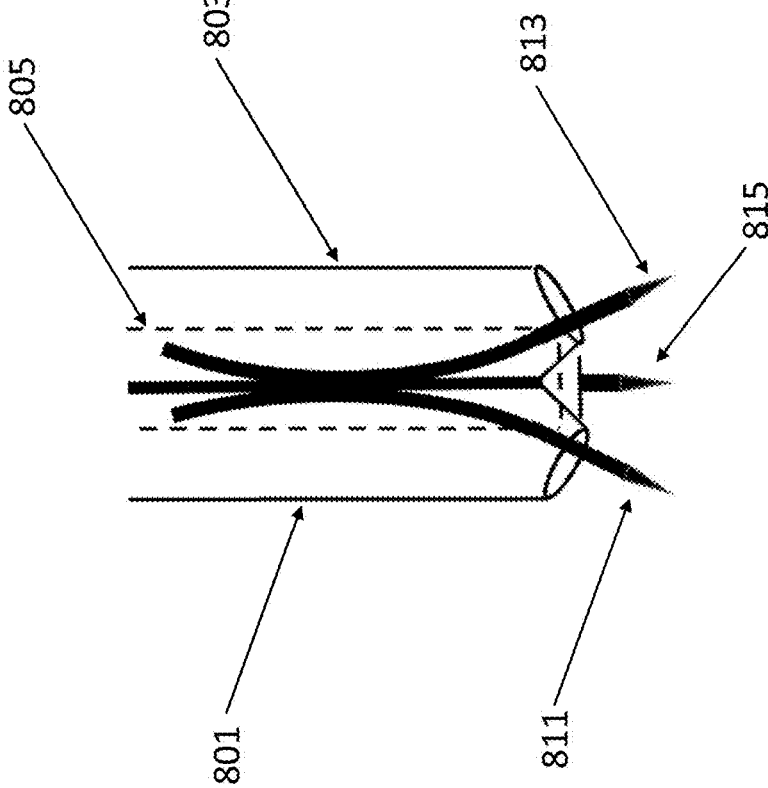
FIG. 8 is an illustration of a catheter device with three lumens, each lumen carrying a needle, according to embodiments.

In embodiments, the catheter device can have more than two lumens. FIG. 8 is an illustration of a catheter device with three lumens 801, 803 and 805, respectively carrying needles 811, 813 and 815, according to embodiments. It can be appreciated based on the present disclosure, that as convenient for a given application, devices with other multiplicities of needles can also be constructed.

Figure 9:
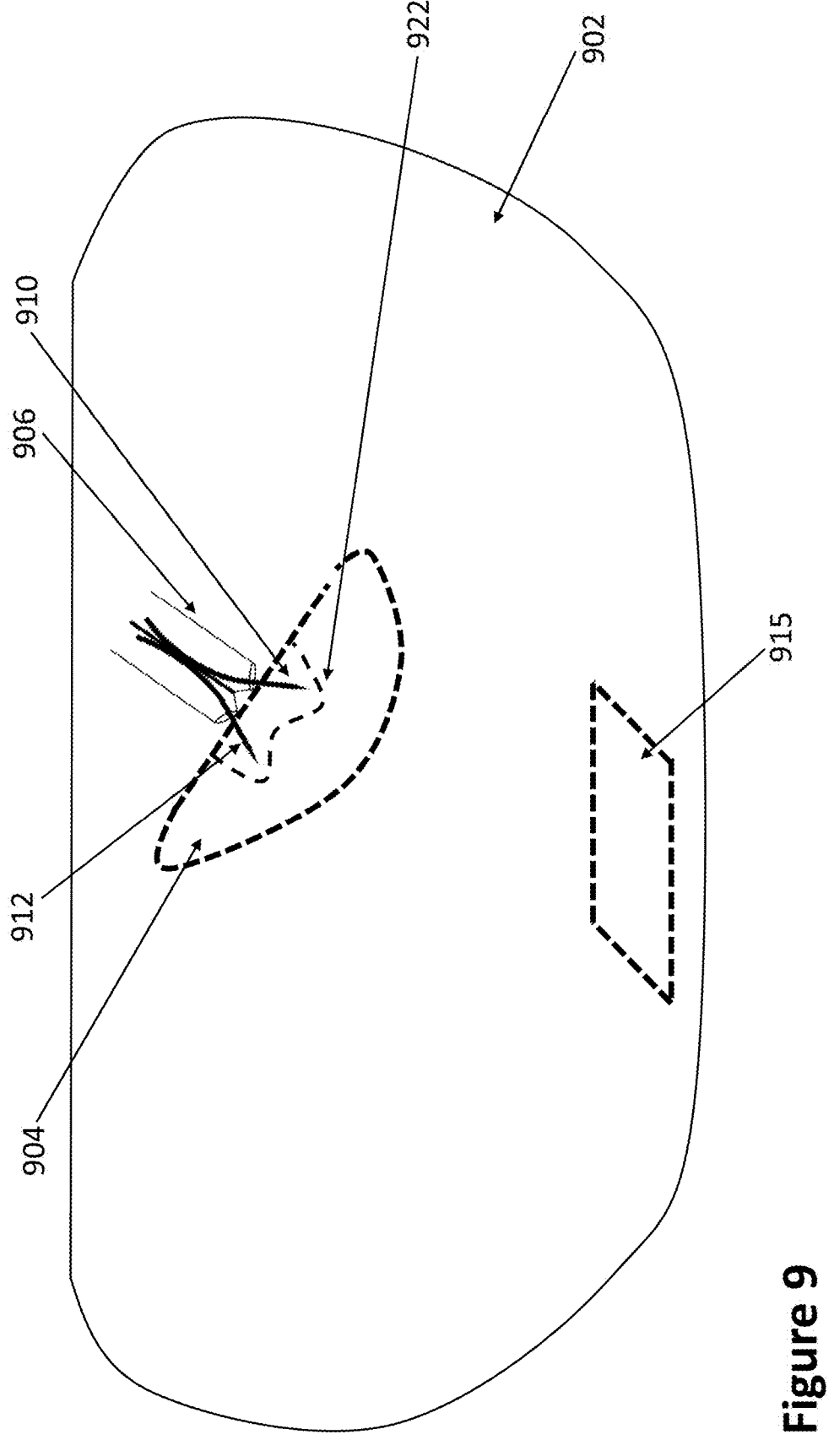
FIG. 9 is an illustration of a catheter device with needles placed in an organ within a subject where irreversible ablation is delivered in unipolar mode with a reference patch, according to embodiments.

The devices disclosed herein are generally positioned such that a given target anatomy can be directly accessed from that position, initially at a tissue surface, and the needles are then extended to penetrate the tissue surface and enter an organ or anatomical structure where therapy delivery is desired. FIG. 9 is an illustration of a catheter device 906 that is placed adjacent to anatomical organ 904 within a subject body 902 (shown in the figure in cross section), according to embodiments. Needles 910 and 912 are extended from the device lumens to penetrate and enter organ 904. In one embodiment, the needles can be used as a single, joint electrode (i.e., polarized with one electrical polarity) and paired electrically with a reference electrode patch 915 (polarized with the opposite electrical polarity) to deliver pulsed field ablation in unipolar (also called monopolar) mode. In other embodiments, the needles 910 and 912 can be used as a bipolar electrode pair for bipolar pulsed field ablation delivery. Application of a pulsed field ablation waveform to the electrodes results in the generation of an electric field and, depending on the tissue irreversible electroporation threshold, a lesion zone such as the zone with boundary 922 is generated as a result of ablation. If a larger treatment volume or region is desired, the needles 910 and 912 can be retracted, the catheter moved to and positioned at a different location, the needles 910 and 912 inserted at the new location and therapy delivered at the new location.

In some embodiments, the catheter devices of the present invention can have an outer diameter in the approximate range of about 0.5 mm to about 5 mm, inclusive of all values and sub-ranges therebetween. In embodiments, the needles or wires can have a diameter in the approximate range of about 0.15 mm to about 1.6 mm, inclusive of all values and sub-ranges therebetween, depending on convenience and/or suitability for a given application.

Figure 10:
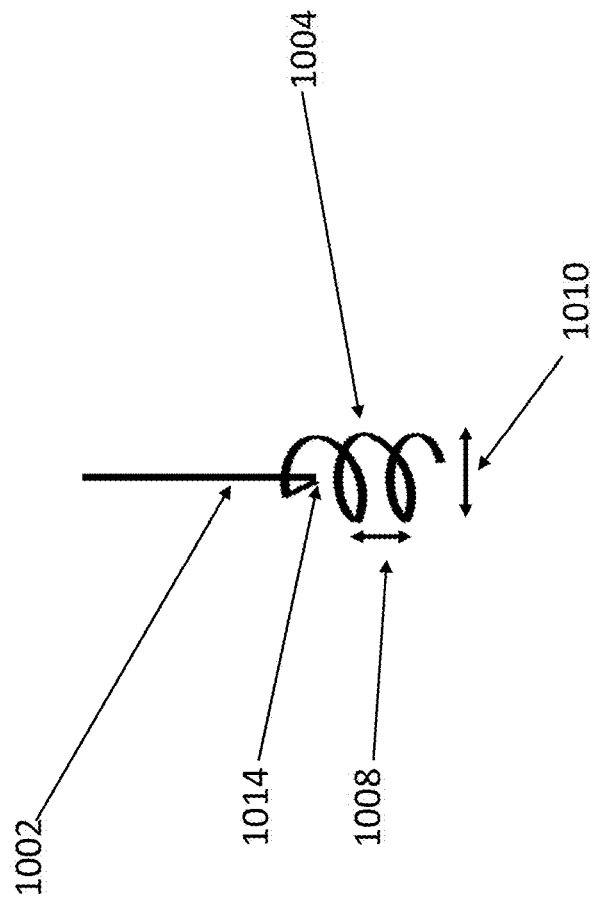
FIG. 10 schematically illustrates a needle wire with a helical distal portion, according to embodiments.

In embodiments, the catheter device of the present disclosure can have a needle wire with a distal portion that is wound as a helix. FIG. 10 schematically illustrates a needle wire 1002 with a helical distal portion 1004, according to embodiments. The helical portion 1004 is characterized by a pitch 1008 and a winding diameter 1010, and the helix is disposed such that the axis of the helix coincides with the tangent to the wire at the point of attachment 1014 of the helix. In this way twists of the wire are translated directly to turns of the helix. In some embodiments, the pitch of the helix can be in the approximate range of between about 0.1 mm and about 4 mm, inclusive of all values and sub-ranges therebetween, and the diameter of the helix (measured on the winding diameter of the centerline) can be in the approximate range of between about 0.3 mm and about 4 mm, inclusive of all values and sub-ranges therebetween.

Figure 11:
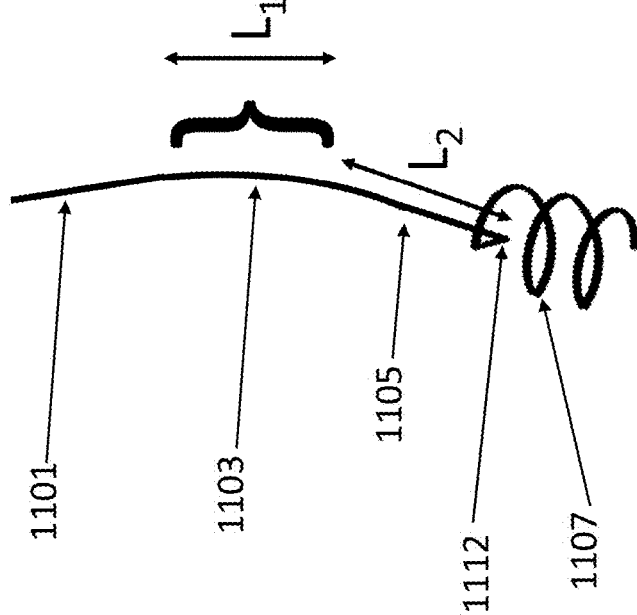
FIG. 11 schematically illustrates a needle wire with a helical distal portion with a slight bend in the shaft of the wire at a location proximal to the helical portion, according to embodiments.

In embodiments, the wire can have a slight bend in a portion proximal to the distal helix. FIG. 11 schematically illustrates a needle wire 1101 with a helical distal portion 1107 with a slight bend in the shaft of the wire over a length LI at an approximate location 1103 proximal to the helical portion and separated from the helix by a length 1105 (also denoted by L2 in the figure), according to embodiments. The helix is disposed such that the axis of the helix coincides with the tangent to the wire at the point of attachment 1112 of the helix. In this way, twists of the wire are translated directly to turns of the helix. In some embodiments, the length L1 of the bend can range approximately between about 3 mm and about 100 mm, inclusive of all values and sub-ranges therebetween, and the length L2 can range approximately between about 5 mm and about 100 mm, inclusive of all values and sub-ranges therebetween.

Figure 12:
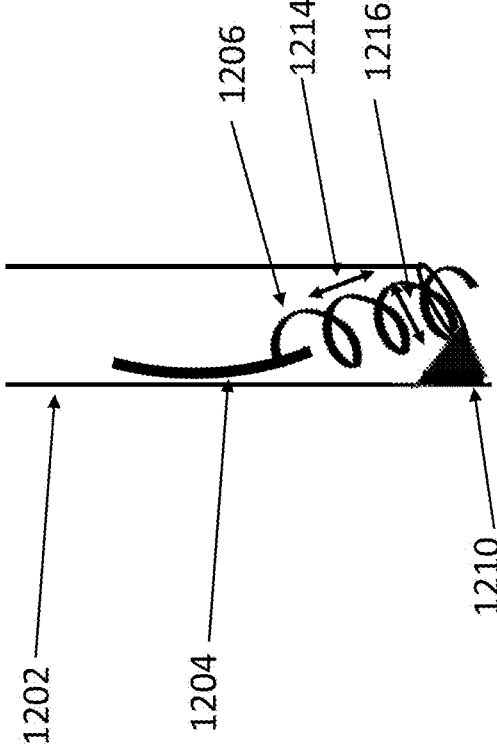
FIG. 12 schematically illustrates a catheter device with a lumen with an internal wedged distal lumen and a needle wire with a helical distal portion, with the helix just emerging from the distal end of the device, according to embodiments.

As illustrated in FIG. 12, in some embodiments, the catheter device 1202 can have a lumen with an internal wedged distal lumen 1210 and a needle wire 1204 with a helical distal portion 1206, where the helix is shown just emerging from the distal end of the device. Within the lumen, the helix is stretched and its pitch 1214 is larger than in the unstressed state while the helix diameter 1216 is smaller than in the unstressed state.

Figure 13:
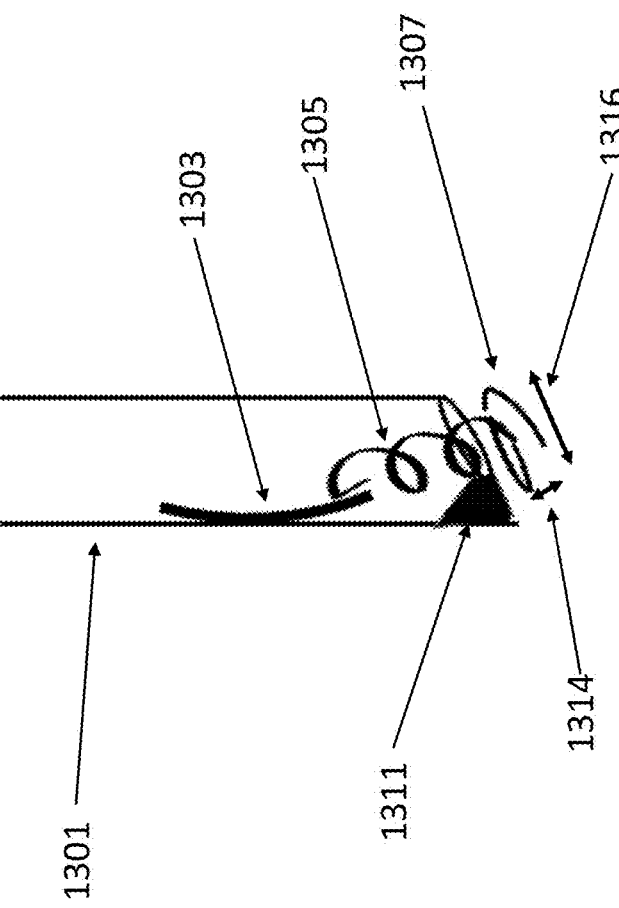
FIG. 13 schematically illustrates a catheter device with a lumen with an internal wedged distal lumen and a needle wire with a helical distal portion, with the helix emerging from the distal end of the device, and with the portion of the helix outside the catheter shaft assuming its unstressed geometry with a larger helix diameter and smaller pitch, according to embodiments.

FIG. 13 schematically illustrates the catheter device 1301, structurally and/or functionally similar to the catheter device 1202, with a lumen with an internal wedged distal lumen 1311 and a needle wire 1303 with a helical distal portion 1305, with the helix emerging from the distal end of the device to a degree greater than that shown in FIG. 12. As depicted in FIG. 13, with more of the helix emerging or extended out from the distal end of the catheter device 1301, the portion of the helix 1307 outside the catheter shaft assumes its unstressed geometry with a larger helix diameter 1316 (e.g., a helix diameter larger than 1216) and a smaller pitch 1314 (e.g., a pitch smaller than pitch 1214) as compared to the stressed (stretched) state within the lumen (e.g., as described with reference to FIG. 12).

Figure 14:
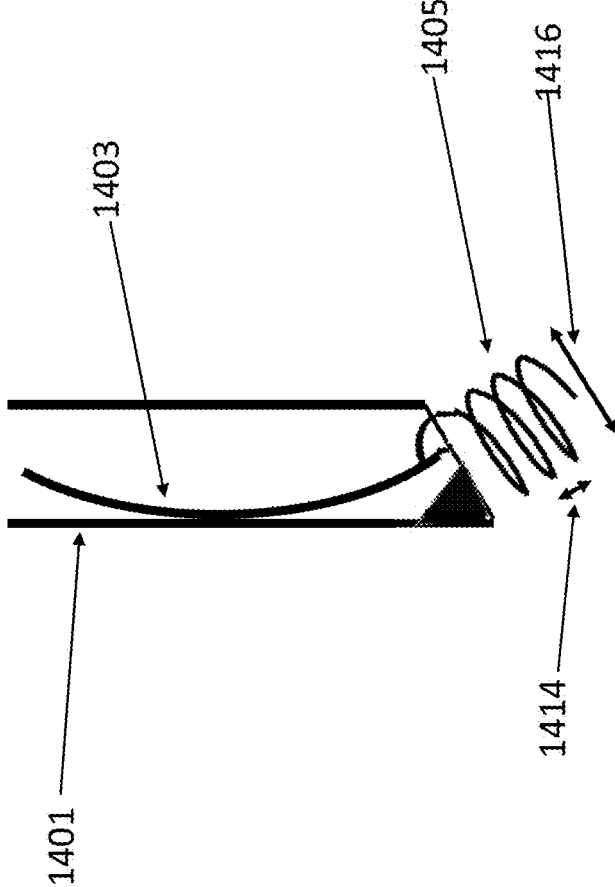
FIG. 14 schematically illustrates a catheter device with a lumen with an internal wedged distal lumen and a needle wire with a helical distal portion, with the helix fully deployed outside the distal end of the device, and with the helix assuming its unstressed geometry with a larger helix diameter and smaller pitch, according to embodiments.

FIG. 14 schematically illustrates a catheter device 1401, structurally and/or functionally similar to the catheter device 1202, with a lumen with an internal wedged distal lumen and a needle wire 1403 with a helical distal portion 1405, with the helix 1405 fully deployed outside the distal end of the device, with the helix assuming its unstressed geometry with a larger helix diameter 1416 (e.g., a helix diameter larger than 1216) and smaller pitch 1414 (e.g., a pitch smaller than pitch 1214) as compared to the stressed (stretched) state of the helix within the lumen.

Figure 15C:
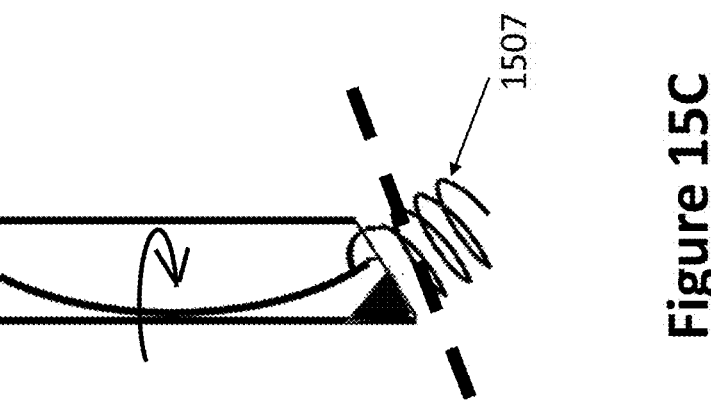
FIGS. 15A, 15B and 15C provide schematic illustrations of a catheter device positioned near a tissue surface with a helical wire being successively deployed so as to puncture the tissue surface and enter a desired organ anatomy with the helical portion fully deployed in the organ beneath the tissue surface, according to embodiments.
Figure 15B:
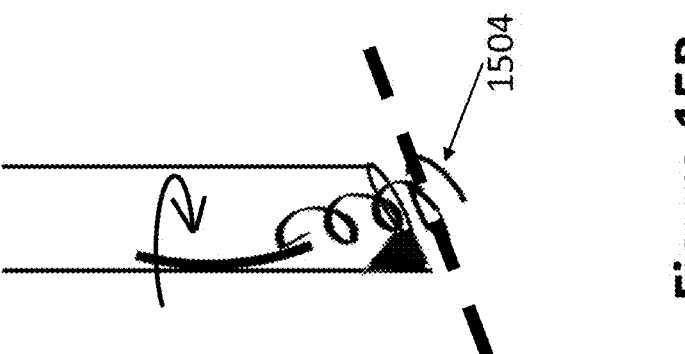
Figure 15A:
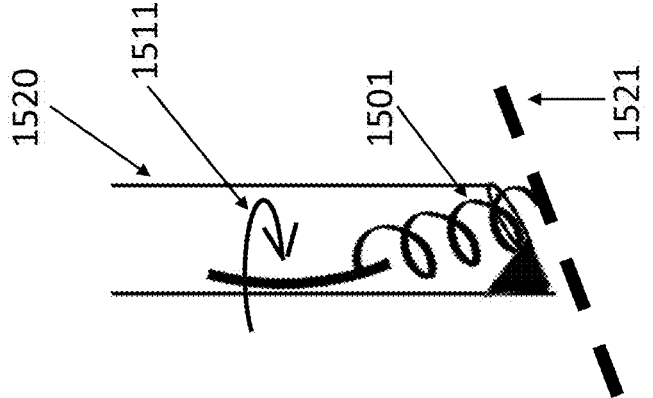

FIGS. 15A, 15B and 15C provide schematic illustrations of a catheter device 1520 positioned near a tissue surface 1521 with a helical wire being successively deployed (1501, 1504, 1507) so as to puncture the tissue surface and enter a desired organ anatomy with the helical portion fully deployed as shown in FIG. 15C in the organ beneath the tissue surface. In the case of a right-handed helix (as shown in FIGS. 15A, 15B, and 15C), clockwise rotation 1511 of the wire as seen from the top together with forward motion serves to advance the helical needle like a corkscrew and anchor it firmly in the tissue. In practice, the helical needle is initially deployed partially in a cavity such as in the stomach or other tubular anatomy with adequate spatial room to permit expansion of the distal portion helix of the helix as it emerges from the lumen. Subsequently, the helical needle is advanced and screwed into tissue wherein it assumes its unstressed state with a larger helix diameter.

Figure 16:
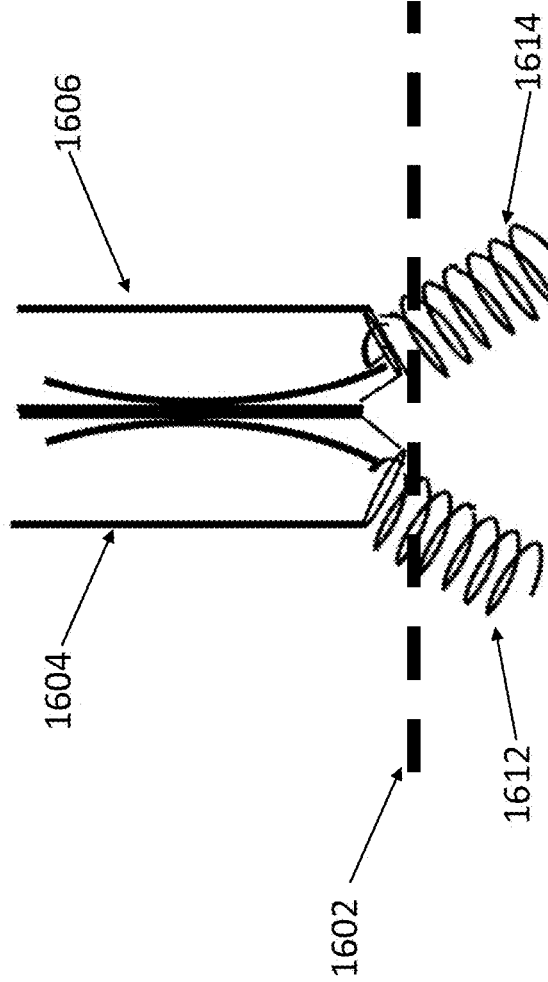
FIG. 16 is a schematic illustration of a catheter device with two lumens each angled away from the catheter long axis at the distal end, each lumen carrying a helical needle wire, positioned near a tissue surface with both helical wires deployed into the tissue surface, according to embodiments.

In embodiments, the catheter device can have two or more lumens each carrying a wire with a helical needle distal portion. FIG. 16 depicts a catheter device with two lumens 1604 and 1606, each angled away from the catheter long axis at the distal end with the catheter positioned at a tissue surface 1602 that it is desired to penetrate, according to embodiments. The lumens 1604 and 1606 respectively carry helical needle wires 1612 and 1614 with both helical wires deployed into the tissue surface 1602. Once deployed suitably in the region of interest (for example, a tumor), irreversible electroporation can be delivered to the needles in either bipolar configuration (needles polarized with opposite polarities) or monopolar configuration (with a reference electrode patch as an oppositely polarized electrode).

In variant embodiments, the catheter device can have more than two lumens with a multiplicity of helical needles or a combination of different numbers of straight needles and helical needles. In other embodiments, the catheter device can have multiple lumens that have a curved distal portion.

Figure 17:
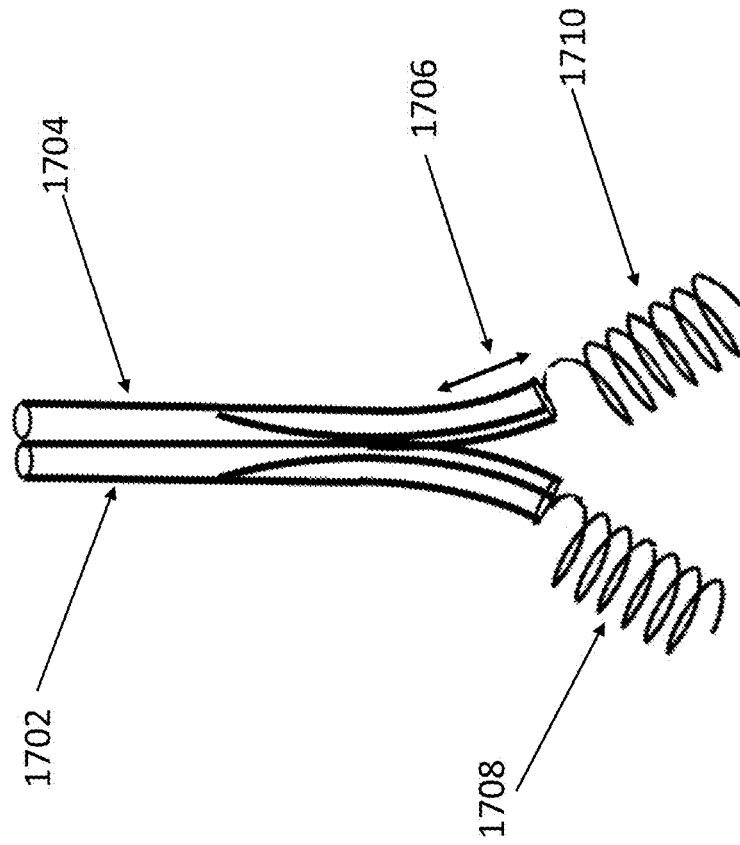
FIG. 17 is a schematic illustration of a catheter device with two lumens with the two lumens curved away from the catheter long axis in their distal portions, each lumen carrying a helical needle wire, according to embodiments.

FIG. 17 shows a schematic illustration of a catheter device with two lumens 1702 and 1704 with the two lumens curved away from the catheter long axis in their distal portions over a length 1706, each lumen 1702 and 1704 carrying respective helical needle wires 1708 and 1710, according to embodiments. In embodiments, the length 1706 can be in the approximate range of between about 3 mm and about 60 mm, inclusive of all values and sub-ranges therebetween. When fully deployed, the angle between the respective helix axes the helices of needles 1708 and 1710 can be in the approximate range of between about 10 and about 75 degrees, inclusive of all values and sub-ranges therebetween.

Figure 18:
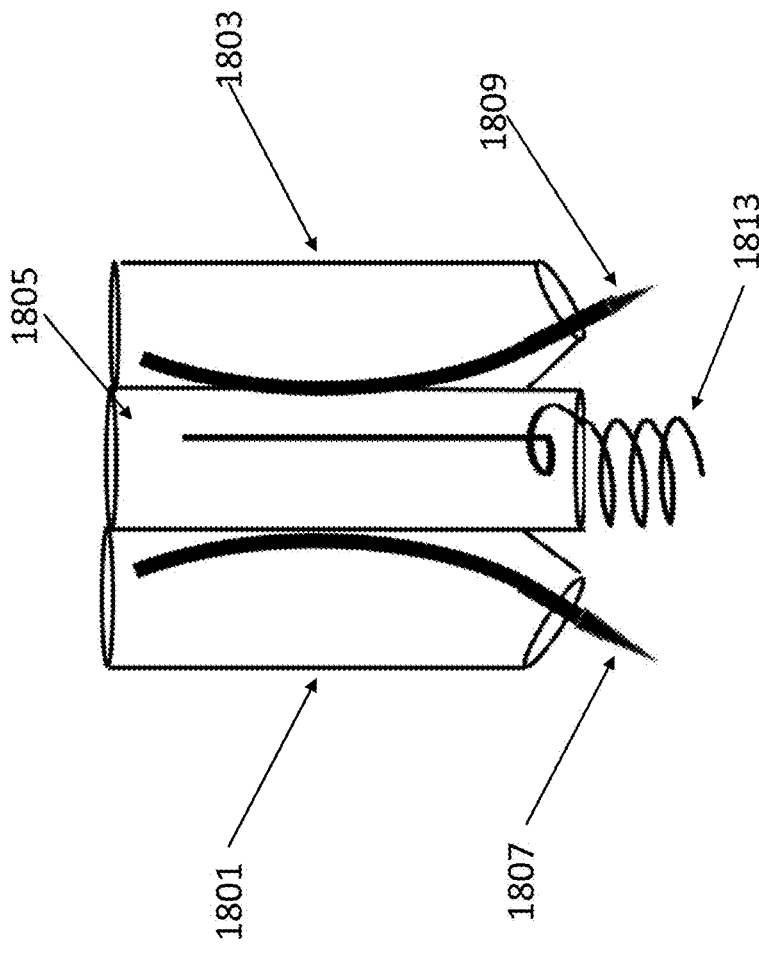
FIG. 18 is a schematic illustration of a catheter device with a central lumen and two outer lumens with the two outer lumens angled away from the catheter long axis in their distal portions, with the central lumen carrying a helical needle wire and the two outer lumens each carrying a needle, according to embodiments.

In embodiments, the catheter device can have a central lumen surrounded by an outer lumen, with the central and outer lumens carrying either straight or helical needles. For example, FIG. 18 illustrates a catheter device with a central lumen 1805 and two outer lumens 1801 and 1803, with the two outer lumens 1801 and 1803 angled away from the catheter long axis in their distal portions, and with the central lumen 1805 carrying a helical needle wire 1813 and the two outer lumens 1801 and 1803 respectively carrying straight needles 1807 and 1809.

Figure 19:
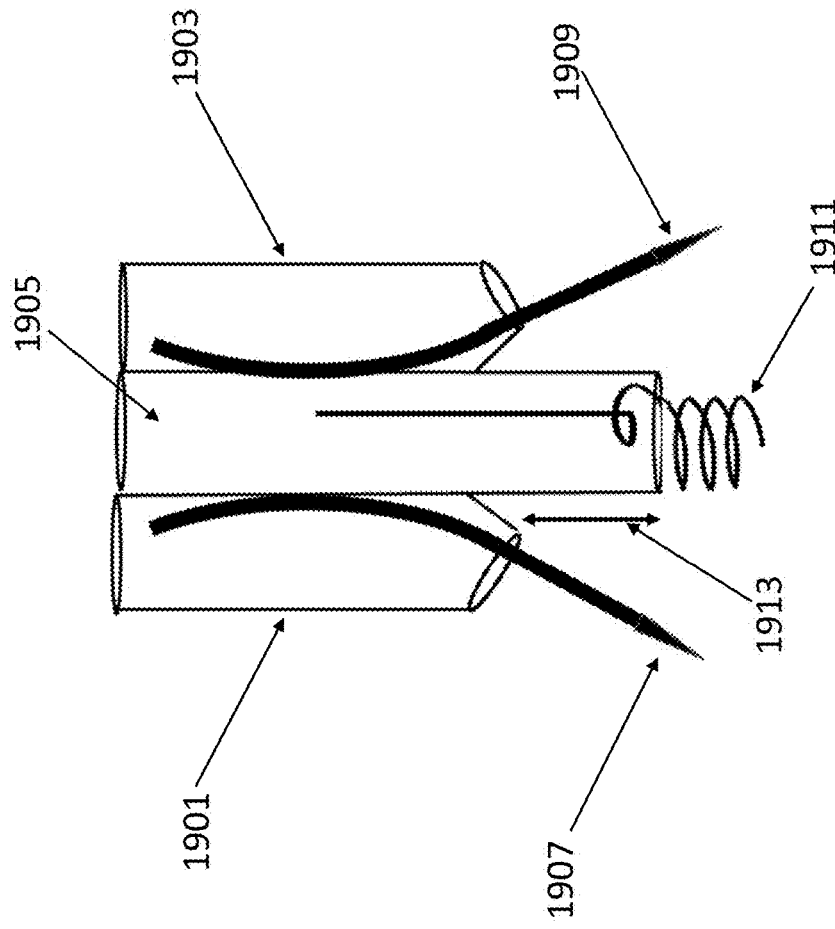
FIG. 19 is a schematic illustration of a catheter device with a central lumen and two outer lumens with the two outer lumens angled away from the catheter long axis in their distal portions, with the central lumen carrying a helical needle wire and the two outer lumens each carrying a needle, and with the distal end of each outer lumen located at a proximal position with respect to the distal end of the central lumen, according to embodiments.

As another example of a variant embodiment, FIG. 19 illustrates a catheter device with a central lumen 1905 and two outer lumens 1901 and 1903, with the two outer lumens 1901 and 1903 angled away from the catheter long axis in their distal portions, and with the central lumen 1905 carrying a helical needle wire 1911 and the two outer lumens 1901 and 1903 carrying respective needles 1907 and 1909, and with the distal end of each outer lumen 1901 and 1903 located at a proximal position separated by a length 1913 with respect to the distal end of the central lumen 1905. The separation length between central and outer lumens in practice can range between about 3 mm and about 60 mm in embodiments, inclusive of all values and sub-ranges therebetween, depending on convenience and/or suitability for the application of interest.

Any of the above embodiments described can be in the form of a deflectable catheter with deflection of the catheter controlled from a control mechanism in the handle and by mechanisms such as the use of pull wires familiar to those skilled in the art of interventional catheters.

In other embodiments, the catheter device of the present invention can be a percutaneous rigid or semi-rigid needle for puncturing tissue and accessing a target site or region where therapy is to be delivered in a minimally invasive surgical procedure performed under image guidance, for example, with CT imaging. For instance, FIG. 20A is a schematic illustration of a percutaneous needle device, according to embodiments, showing a needle shaft 2001 ending in a distal tip with curved, sharp edges 2021 and 2023 shaped for puncturing a tissue surface. The needle shaft has two lumens 2003 and 2005, with the lumens respectively carrying helical needle wires 2009 and 2011. The lumens 2003 and 2005 exit the side of the needle shaft 2001 at respective openings 2015 and 2017, from where the helical needles can be deployed.

Figure 20B:
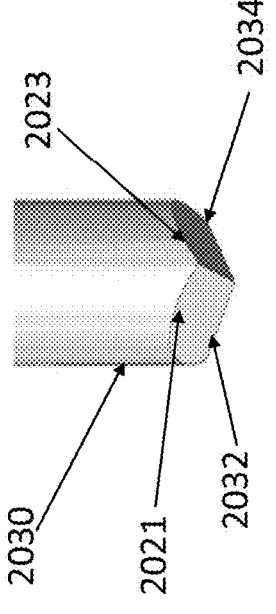
FIG. 20B is a three-dimensional rendering of the distal portion of the needle shaft of the device shown in FIG. 20A.
Figure 20A:
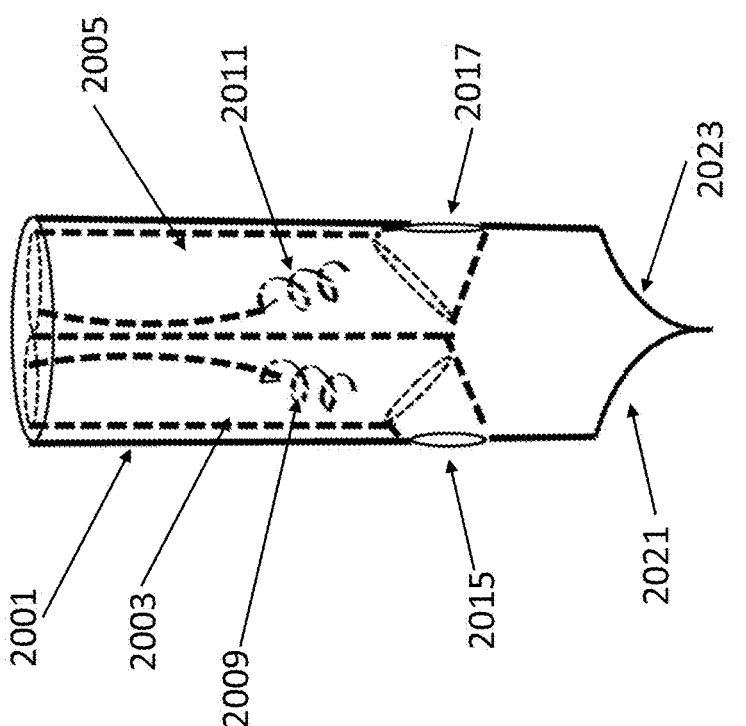
FIG. 20A is a schematic illustration of a percutaneous needle device, showing a needle shaft ending in a distal tip that is shaped for puncturing a tissue surface, the needle shaft having two lumens, with each lumen carrying a helical needle wire, according to embodiments.

FIG. 20B is a three-dimensional rendering of the distal portion of the needle shaft of the device shown in FIG. 20A, showing the distal needle portion 2030 and the curved, sharp edges 2021 and 2023 bounding planar faces 2032 and 2034. In use, the helical wires are initially in their respective lumens. The needle shaft 2001 is used to puncture tissue and is advanced to the region of interest under appropriate image guidance, for example, with CT imaging. Once at the desired site, the helical needles 2009 and 2011 are advanced.

Figure 21:
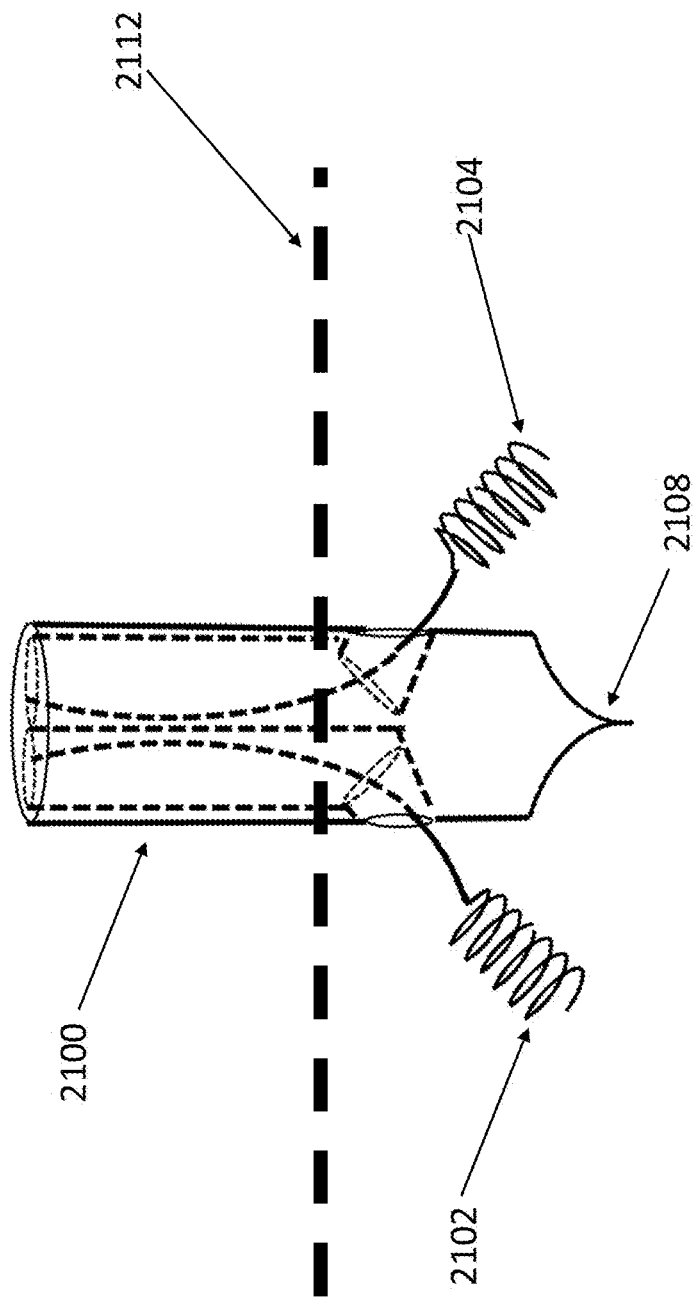
FIG. 21 is a schematic illustration of a percutaneous needle device, showing a needle shaft ending in a distal tip that is shaped for puncturing a tissue surface, the needle shaft having two lumens, with each lumen carrying a helical needle wire, with the needle shaft as well as the helical wires fully inserted into and engaging tissue, according to embodiments.

FIG. 21 is a schematic illustration of a percutaneous needle device, according to embodiments, showing a needle shaft 2100 ending in a distal tip 2108 that is shaped for puncturing a tissue surface 2112, the needle shaft having two lumens, with each lumen carrying a helical needle wire 2102 and 2104, with the needle shaft as well as the helical wires 2102 and 2104 fully inserted into and engaging tissue. In such an application, where the distal tip 2108 of the needle shaft 2100 is disposed below the tissue surface 2112, there may not be much difference in geometry between the undeployed (e.g., stretched) and deployed (e.g., unstressed) state of the helical needle, as any expansion/relaxation of the helix is limited by the tissue. In embodiments for this use case, the helix diameter can closely or approximately match the internal diameter of the lumen of the catheter, or it can be a little smaller than the internal diameter of the catheter lumen.

Figure 22A:
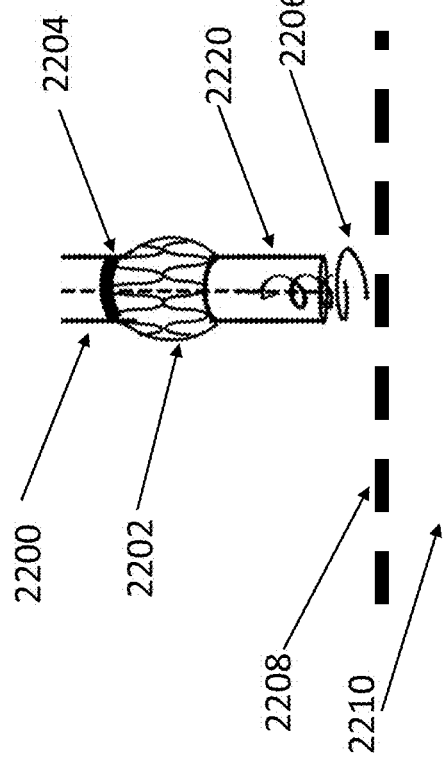
FIG. 22A is a schematic illustration of a catheter device situated proximal to a tissue interface, showing a catheter shaft with a lumen carrying a helical needle wire, with the helical needle wire emerging from the distal end of the catheter shaft proximal to a tissue interface, and with the catheter shaft having a compressible electrode mounted proximal to the distal end of the catheter shaft, according to embodiments.

FIG. 22A is a schematic illustration of a catheter device 2200 with a catheter shaft 2220 and with a lumen carrying a helical needle device or wire 2206, according to embodiments. The catheter device 2200 can have a compressible electrode 2202 mounted proximal to the distal end of the catheter shaft 2220. In embodiments, the compressible electrode 2202 can have a collar portion 2204 to facilitate mounting the electrode on the shaft. The collar portion 2204 can be crimped or swaged onto the catheter shaft 2220 in a manner familiar to those skilled in the art. In embodiments, the compressible electrode 2202 can comprise a cage-like structure made of a highly elastic, electrically conducting material, such as, for example, Nitinol. In the figure, the catheter device 2200 is shown with its distal end located proximal to and/or adjacent to a tissue interface 2208, wherein tissue 2210 on the distal side of the interface may be part of a distinct anatomical organ. In some clinical applications, the proximal side of the tissue interface can comprise the interior space of an anatomical passageway, for example, a portion of the digestive tract or a portion of the airways or tracheal tubes of the lung. As described in the foregoing, the helical needle device 2206 is configured such that, in its unstressed state, the helical portion of the helical needle device 2206 has a helix diameter that is larger than the internal diameter of the catheter device 2200. When the helical portion is inside the catheter shaft 2220, it is stressed or constrained by the catheter shaft 2220 to have a helix diameter that is smaller than the helix diameter in its unstressed state. Thus, as the helical needle device 2206 emerges from the shaft 2220 proximal to the tissue interface 2208, the helix portion expands in diameter. In embodiments, the distal tip of the helical needle wire 2206 is suitably sharpened for ease of penetration and advancement into tissue.

Figure 22B:
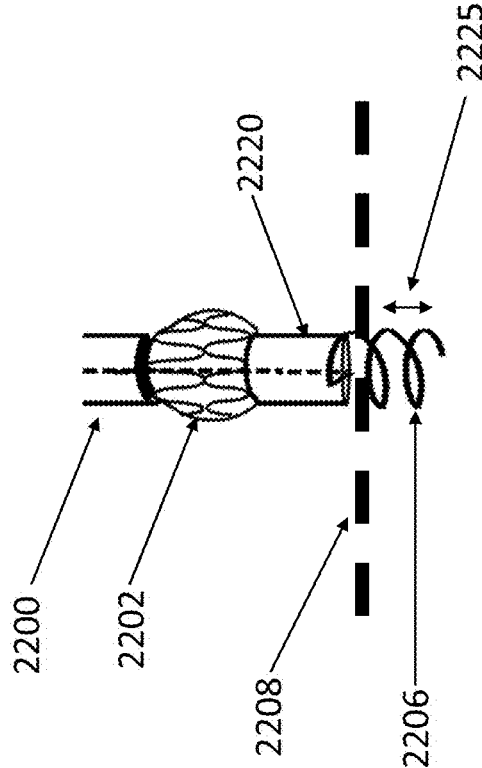
FIG. 22B is a schematic illustration of a catheter device situated proximal to a tissue interface, showing a catheter shaft with a lumen carrying a helical needle wire, with the helical needle wire emerging from the distal end of the catheter shaft and penetrating a tissue interface, and with the catheter shaft having a compressible electrode mounted proximal to the distal end of the catheter shaft, according to embodiments.
Figure 27:
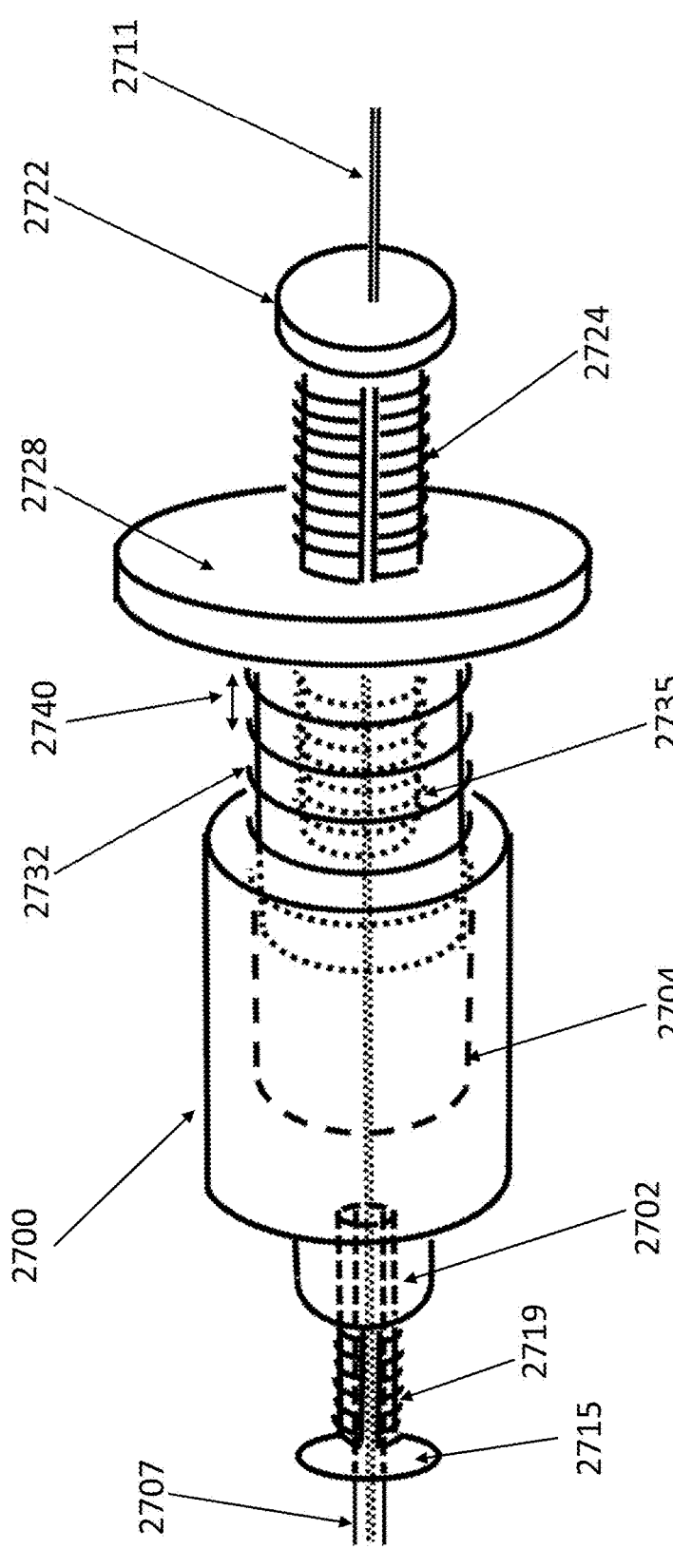
FIG. 27 is a schematic illustration of a clasping device for clasping both a catheter and a needle device of the present disclosure so as to provide a means of making controlled movements of the needle device relative to the catheter device, according to embodiments.

In use, once the tissue interface is engaged (for example, under ultrasound visualization), the needle device 2206 is rotated and advanced at the same time such that the needle device 2206 is advanced helically into tissue. One embodiment of a device for rotating and advancing the needle device 2206 is illustrated in FIG. 27 and is further discussed below. FIG. 22B shows the helical needle device completely released or deployed outside the catheter shaft 2220 such that the helical needle device 2206 has been helically advanced into tissue after penetrating the tissue interface 2208. The figure shows the catheter device 2200 with the shaft electrode 2202, with the helical needle 2206 located in the tissue anatomy distal to the tissue interface 2208. In use, the distal end of the catheter device 2200 is positioned in an interior anatomical space as described in the foregoing, and as the helical needle device 2206 is deployed in the interior space, it expands to its unstressed dimensions as it exits the catheter shaft 2220. Thus, the pitch 2225 of the helical portion of the needle device 2206 distal to the distal interface corresponds to the helical pitch in the unstressed or reference state of the needle device 2206. In embodiments, the helix diameter of the helical needle device 2206 in its unstressed state can lie in the range between approximately 0.5 mm and approximately 10 mm, including all ranges and values therebetween, while the helix pitch of the helical needle device 2206 in its unstressed state can lie in the range between approximately 0.3 mm and approximately 6 mm, including all ranges and values therebetween. In embodiments, the length of the helix (measured along the central axis of the helix) in the unstressed state can lie in the range between approximately 3 mm and approximately 50 mm, including all ranges and values therebetween, and any portion of the length of the helix can penetrate a tissue or organ for the delivery of ablation therapy.

Once the needle device 2206 is suitably positioned in the tissue of interest targeted for ablation, in embodiments, the interior anatomical space in which the shaft electrode 2202 is situated may be filled with saline or similar electrically conducting fluid. Ablation therapy is delivered in the form of high voltage pulses applied between the helical needle device 2206 and the shaft electrode 2202 with these two electrodes electrically configured with opposite electrical polarities. In embodiments, the helical needle device 2206 can comprise an electrically conducting hyper-elastic material, such as, for example, Nitinol. While the helical portion of the needle device 2206 is electrically conducting, the length of the needle device 2206 proximal to the helical portion can be electrically insulated. The shaft electrode 2202 is connected to an insulated lead wire for electrical conduction. In embodiments, the ablation therapy delivery can comprise high voltage pulses with a voltage difference of at least about 300 Volts and up to about 10,000 Volts between oppositely polarized electrodes, including all ranges and values therebetween. The applied potential difference across electrodes results in the generation of an electric field in tissue. Depending on the applied voltage waveform and tissue type, any tissue subject to an electric field larger than a threshold value is killed or ablated by the mechanism of irreversible electroporation.

FIG. 27 illustrates a widget or tool (e.g., a proximal actuation assembly) for the rotation and advancement of a helical needle wire 2711 (e.g., any of the helical needle wires or devices described herein), according to embodiments. The tool can rotate and advance the helical needle wire such that the helical distal portion of the needle wire is advanced helically in a screw-like fashion into the tissue of interest. In embodiments, a catheter device including the helical needle wire (e.g., any of the catheters or catheter devices described herein) may be directly positioned in an anatomical region. Alternatively, in other embodiments, the catheter device can be passed through a working channel of a primary device, such as, for example, an endoscope or bronchoscope (not shown in the figure), and then be placed in an anatomical region. In embodiments, the catheter device can be placed under visual guidance (e.g., via optical or ultrasound imaging) through the endoscope. Once the catheter device is suitably positioned in the anatomy, a first proximal screw 2715 can be inserted over the proximal end of the catheter device 2707 that is accessible to a user, e.g., directly outside a subject anatomy or outside a primary device such as an endoscope. The screw 2715 has a longitudinally split screw portion 2719 that is configured to fit closely over a catheter 2707 of the catheter device such that, when it is screwed into a threaded cavity 2702 of a hub 2700 of the catheter device 2707, it grips the catheter 2707 tightly. The needle wire 2711 extends out of the proximal end of the catheter 2707 through the hub 2700. A second proximal screw 2722 can be inserted over the proximal end of the needle wire 2711 together with a hub screw 2728. The screw 2722 has a longitudinally split screw portion 2724 configured to fit closely over the needle wire 2711 such that when it is screwed into a threaded cavity 2735 of the hub screw 2728, it grips the needle wire 2711 tightly. In this manner, the first proximal screw 2715 is effectively secured to or coupled to the catheter 2707 while the second proximal screw 2722 is effectively secured to or coupled to the needle wire 2711. The hub screw 2728 can be screwed into a threaded cavity 2704 in the hub 2700 as the hub 2700 is held in place, thereby holding the catheter 2707 in place. Specifically, in use, the needle wire's distal end is situated at a tissue interface and, once it is ready to be advanced into tissue, the hub screw 2728 is screwed into threaded cavity 2704 while the hub 2700 is held in place. In some embodiments, the pitch 2740 of the helical screw 2732 is identical to the helical pitch 2225 of the needle wire 2711 in its unstressed or refence state (shown and described above with reference to FIG. 22B). Thus, one rotation of the hub screw 2728 into threaded cavity 2704 advances the distal end of the helical needle wire 2711 by one helical turn into tissue. In this manner, the needle wire 2711 can be helically advanced into tissue until its distal tip is at a desired or predefined depth in tissue, as can be confirmed, for example, from an ultrasound image. After placement at a suitable target location, high voltage pulsed field ablation therapy can be delivered (e.g., as described in the foregoing) by the application of high voltage pulses to the needle wire 2711 and to an (electrically paired) shaft electrode (e.g., any of the shaft electrodes described herein). In alternate embodiments, a reference patch can be electrically paired with the needle wire 2711 for ablation delivery in unipolar mode. In embodiments, multiple ablations can be delivered at a given target location. Subsequently, the helical needle wire 2711 can be retracted by unscrewing the hub screw 2728, whereupon the helical needle wire 2711 retraces its path in tissue and is withdrawn from the tissue and tissue interface.

Optionally, the catheter and/or the primary device, such as an endoscope or bronchoscope, is steered to reposition the distal end of the catheter 2707 for access to a new target location in tissue, and the process can be repeated as desired.

Figure 23:
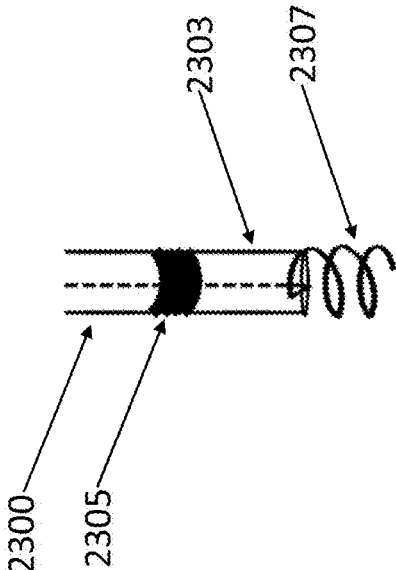
FIG. 23 is a schematic illustration of a catheter device showing a catheter shaft with a lumen carrying a helical needle wire, with the helical needle wire protruding from the distal end of the catheter shaft, and with the catheter shaft having a ring electrode mounted proximal to the distal end of the catheter shaft, according to embodiments.

FIG. 23 is a schematic illustration of a catheter device 2300 showing a catheter shaft 2303 with a lumen carrying a helical needle or wire 2307, according to embodiments. The helical needle 2307 is shown protruding from the distal end of the catheter shaft 2303. The catheter shaft can have a ring electrode 2305 mounted proximal to the distal end of the catheter shaft 2305, according to embodiments. The helical needle 2307 and the shaft electrode 2305 can be electrically paired with opposite electrical polarities and be configured as a bipolar electrode pair for pulsed field ablation delivery. The helical needle 2307 can be inserted into tissue by helical advancement with a suitable tool at the proximal end of the catheter device 2300, e.g., as described with respect to FIG. 27.

Figure 24:
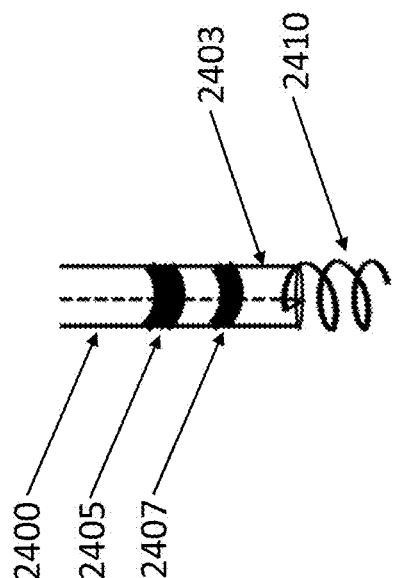
FIG. 24 is a schematic illustration of a catheter device showing a catheter shaft with a lumen carrying a helical needle wire, with the helical needle wire protruding from the distal end of the catheter shaft, and with the catheter shaft having two ring electrodes mounted proximal to the distal end of the catheter shaft, according to embodiments.

FIG. 24 is a schematic illustration of a catheter device 2400 showing a catheter shaft 2403 with a lumen carrying a helical needle or wire 2410, according to embodiments. The helical needle 2410 is shown protruding from the distal end of the catheter shaft 2403. The catheter shaft 2403 can have two ring electrodes 2405 and 2407 mounted proximal to the distal end of the catheter shaft, according to embodiments. The helical needle 2410 and the shaft electrodes 2405 and 2407 can be electrically paired with opposite electrical polarities and be configured as a bipolar electrode pair for pulsed field ablation delivery. For example, the helical needle 2410 can have one electrical polarity while the electrodes 2405 and 2407 can both have the opposite electrical polarity. The helical needle 2410 can be inserted into tissue by helical advancement with a suitable tool at the proximal end of the catheter device 2400, e.g., as described with respect to FIG. 27.

Figure 25:
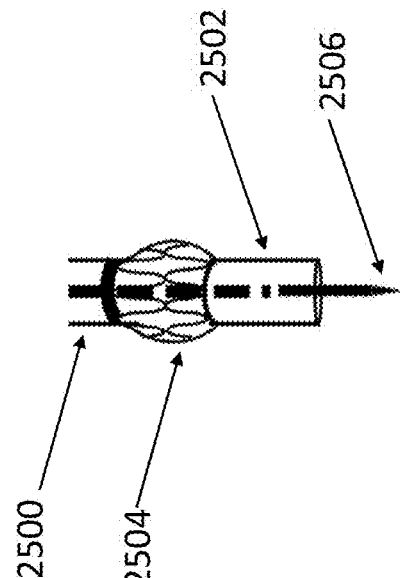
FIG. 25 is a schematic illustration of a catheter device showing a catheter shaft with a lumen carrying a needle device, with the needle device protruding from the distal end of the catheter shaft, and with the catheter shaft having a compressible electrode mounted proximal to the distal end of the catheter shaft, according to embodiments.

FIG. 25 is a schematic illustration of a catheter device 2500 showing a catheter shaft 2502 with a lumen carrying a needle device 2506, according to embodiments. The needle device 2506 is shown protruding from the distal end of the catheter shaft 2502. The catheter shaft 2502 has a compressible electrode 2504 mounted proximal to the distal end of the catheter shaft 2502, according to embodiments. The needle device 2506 can be a straight needle that is configured to penetrate a tissue interface and extend into an anatomical organ for placement at a target site for the delivery of ablation therapy. Once placed at a target location, the needle device 2506 and the shaft electrode 2504 can be electrically paired with opposite electrical polarities and be configured as a bipolar electrode pair for pulsed field ablation delivery. In embodiments, the needle device 2506 can have an exposed electrically conducting surface or portion that is disposed beyond the distal end of the catheter shaft 2502 with a length in the range between approximately 3 mm and approximately 50 mm, including all ranges and values therebetween. In embodiments, the maximum diameter of the exposed electrically conducting portion of the needle device 2506 can lie in the range between approximately 0.1 mm and approximately 2.5 mm, including all ranges and values therebetween. In embodiments, the distal exposed electrically conducting portion of the needle device 2506 can comprise a hyper-elastic material, such as, for example, Nitinol. Proximal to the distal exposed electrically conducting portion, the needle device 2506 can be electrically insulated.

Figure 26:
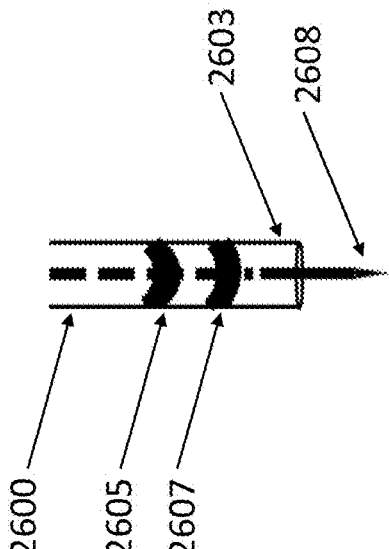
FIG. 26 is a schematic illustration of a catheter device showing a catheter shaft with a lumen carrying a needle device, with the needle device protruding from the distal end of the catheter shaft, and with the catheter shaft having two ring electrodes mounted proximal to the distal end of the catheter shaft, according to embodiments.

FIG. 26 is a schematic illustration of a catheter device 2600 showing a catheter shaft 2603 with a lumen carrying a needle device 2608, according to embodiments. The needle device 2608 is shown protruding from the distal end of the catheter shaft. The catheter shaft 2603 has ring electrodes 2605 and 2607 mounted proximal to the distal end of the catheter shaft 2603, according to embodiments. The needle device 2608 can be a straight needle that is configured to penetrate a tissue interface and extend into an anatomical organ for placement at a target site for the delivery of ablation therapy. Once placed at a target location, the needle device 2608 and the shaft electrodes 2605 and 2607 can be electrically paired with opposite electrical polarities and be configured as a bipolar electrode pair for pulsed field ablation delivery.

In embodiments, the ring electrodes on the catheter shaft of the present disclosure can have outside diameters in the range between approximately 0.5 mm and approximately 6 mm, including all ranges and values therebetween. In embodiments, the compressible electrodes of the present disclosure, such as, for example, electrode 2202 in FIG. 22A and electrode 2504 in FIG. 25, can have an expanded or unstressed diameter in the range between approximately 0.6 mm and approximately 10 mm, including all ranges and values therebetween. When the compressible electrode is disposed within a lumen or channel of another device (e.g., endoscope) having a smaller diameter, the compressible electrode can be compressed or restricted to the smaller diameter of that other device, and as the electrode emerges from inside the lumen or channel of smaller diameter in the other device, the electrode can expand to the diameter of its unstressed state. The shaft electrodes of the present disclosure are electrically connected to insulated lead wires. In embodiments, the lead wires of the shaft electrodes and the needle device can have sufficient insulation to sustain a voltage difference of at least about 500 Volts between them without dielectric breakdown. In alternate embodiments, the insulation of the lead wires and the needle device can sustain a voltage difference of up to about 2000 Volts, up to about 3000 Volts, up to about 4000 Volts, up to about 6000 Volts, or up to about 10,000 Volts between one another without dielectric breakdown.

Figure 28:
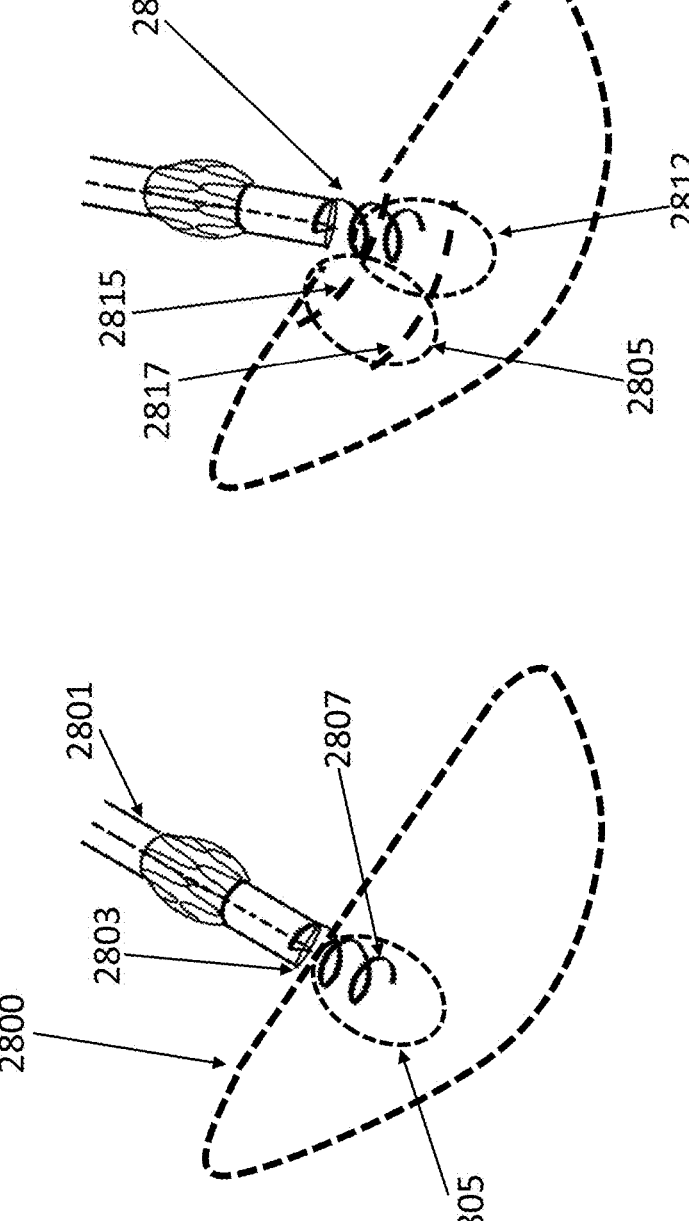
FIG. 28 is a schematic illustration of the process of making overlapping or contiguous ablation lesions with a catheter device of the present disclosure after generating a first ablation zone, according to embodiments, by repositioning the catheter device before tissue penetration with a needle wire so as to permit the generation of a second ablation zone that overlaps or is contiguous to the first ablation zone.

FIG. 28 is a schematic illustration of the process of making overlapping or contiguous ablation lesions with a device 2801 of the present disclosure, according to embodiments. The device 2801 can be used to generate a first ablation zone 2805. After generating the first ablation zone 2805, the device 2801 can be repositioned before tissue penetration with a needle device or wire of the device 2801 so as to permit the generation of a second ablation zone 2812. The second ablation zone 2812 can overlap with or be contiguous to the first ablation zone 2805. In FIG. 28, the image on the left shows the catheter device 2801 in a first position 2803 in a tissue or organ anatomy 2800, with a needle device 2807 penetrating the organ anatomy to generate the first ablation zone 2805. Subsequently, the catheter device 2801 is repositioned to a second position 2810, as shown in the image on the right, and the needle device 2807 inserted into tissue and the second ablation zone 2812 is generated as indicated in the figure. The second ablation zone 2812 is contiguous to or overlaps with the first ablation zone 2805, so that a contiguous volume of tissue is ablated. For instance, the region of tissue between arcs 2815 and 2817 is completely ablated with the overlapping ablation zones 2805 and 2812.

The systems, devices, and methods described herein can be embodied in one or more embodiments, as set forth below.

Embodiment 1: A catheter device with at least one lumen for passage of a needle device, wherein the distal end of the lumen is configured such that the needle device exits the lumen at the distal end of the device at a non-zero angle with respect to the long axis of the catheter, and where the distal portion of the needle comprises an exposed electrical conductor for the passage of an electrical current to tissue upon high voltage application.

Embodiment 2: A catheter device with at least two lumens for passage of a needle device through each lumen, wherein the distal end of at least one lumen is configured such that the needle device exits the lumen at the distal end of the device at a non-zero angle with respect to the long axis of the catheter, and where the distal portion of each needle comprises an exposed electrical conductor for the passage of an electrical current to tissue upon high voltage application.

Embodiment 3: The catheter device of Embodiment 1, where the needle engages tissue for high voltage delivery in unipolar mode.

Embodiment 4: The catheter device of Embodiment 2, where the needles engage tissue for high voltage delivery in bipolar mode.

Embodiment 5: A catheter device with at least one lumen for passage of a helical-tipped needle device, wherein the distal end of the lumen is configured such that the needle device exits the lumen at the distal end of the device at a non-zero angle with respect to the long axis of the catheter, and wherein the distal portion of the needle device is configured in a helical geometry and comprises an exposed electrical conductor for the passage of an electrical current to tissue upon high voltage application.

Embodiment 6: A catheter device with at least two lumens for passage of a helical-tipped needle device through each lumen, wherein the distal end of at least one lumen is configured such that the needle device exits the lumen at the distal end of the device at a non-zero angle with respect to the long axis of the catheter, and wherein the distal portion of each needle device is configured in a helical geometry and comprises an exposed electrical conductor for the passage of an electrical current to tissue upon high voltage application.

Embodiment 7: The catheter device of Embodiment 5, wherein the diameter of the helical geometry of the needle in an unconstrained state is larger than the diameter of the helical geometry of the needle when constrained within the lumen of the catheter.

Embodiment 8: The catheter device of Embodiment 6, wherein the diameter of the helical geometry of each needle in an unconstrained state is larger than the diameter of the helical geometry of that needle when constrained within the lumen of the catheter.

Embodiment 9: A catheter device with at least one lumen for passage of a helical-tipped needle device, wherein the distal portion of the needle device is configured in a helical geometry and comprises an exposed electrical conductor for the passage of an electrical current to tissue upon high voltage application.

Embodiment 10: The catheter device of Embodiment 9, wherein the diameter of the helical geometry of the needle in an unconstrained state is larger than the diameter of the helical geometry of the needle when constrained within the lumen of the catheter.

Embodiment 11: A catheter device with at least two lumens for passage of a needle device through each lumen, a first lumen carrying a first needle device with a substantially straight distal geometry and a second lumen carrying a second needle device with its distal portion configured in a helical geometry, wherein the distal portion of each needle device comprises an exposed electrical conductor for the passage of an electrical current to tissue upon high voltage application.

Embodiment 12: The catheter device of Embodiment 11, where at least a subset of the needle devices engages tissue for high voltage delivery in unipolar mode.

Embodiment 13: The catheter device of Embodiment 11, where at least a subset of the needle devices engages tissue for high voltage delivery in bipolar mode.

Embodiment 14: The catheter device of Embodiment 11, where the catheter device is positioned through the working channel of an endoscope to an anatomical region of interest.

Embodiment 15: The catheter device of Embodiment 9, where the catheter device is positioned through the working channel of an endoscope to an anatomical region of interest.

Embodiment 16: The catheter device of Embodiment 6, where the catheter device is positioned through the working channel of an endoscope to an anatomical region of interest.

Embodiment 17: The catheter device of Embodiment 1, where the catheter device is positioned through the working channel of an endoscope to an anatomical region of interest.

Embodiment 18: The catheter device of Embodiment 11, wherein the diameter of the helical geometry of the second needle device in an unconstrained state is larger than the diameter of the helical geometry of said needle when constrained within the second lumen of the catheter.

Embodiment 19: A method of delivering high voltage pulsed field ablation therapy to tissue, comprising the positioning of a catheter device at an anatomical region of interest, passing a first needle device through a first lumen of the catheter device to puncture a tissue of interest and advancing the first needle device within the tissue of interest to position its distal tip at a target location, passing a second needle device through a second lumen of the catheter device to puncture a tissue of interest, and advancing the second needle device within the tissue of interest to position its distal tip at a target location, and applying high voltage pulses to the needle devices to deliver ablation therapy, the distal portion of each needle device comprising an exposed electrical conductor for the passage of an electrical current to tissue upon high voltage application.

Embodiment 20: The method of Embodiment 19, wherein the high voltage pulses are applied in bipolar fashion between the first and second needle devices.

Embodiment 21: The method of Embodiment 19, wherein the distal portion of at least one of the needle devices is configured in a helical geometry and comprises an exposed electrical conductor for the passage of an electrical current to tissue upon high voltage application.

Embodiment 22: The method of Embodiment 21, wherein the diameter of the helical geometry of the at least one needle device with a helical distal geometry in an unconstrained state is larger than the diameter of the helical geometry of said needle device when constrained within the lumen of the catheter.

Embodiment 23: The method of Embodiment 19, where the catheter device is positioned at an anatomical region of interest by passage through a channel of an endoscopic device.

Embodiment 24: A catheter device with a shaft and a lumen for passage of a needle device, where the longitudinal section of the distal portion of the needle comprises a substantially straight geometry, where the distal portion of the needle comprises an exposed electrical conductor for the passage of an electrical current to tissue upon high voltage application for pulsed field ablation delivery, and where the length of the needle proximal to the distal portion is electrically insulated, with the insulation capable of withstanding a voltage of at least 500 Volts without dielectric breakdown.

Embodiment 25: The catheter device of Embodiment 24, with the distal portion of the shaft of the catheter including at least one shaft electrode that has an electrical polarity opposite to that of the needle during pulsed field ablation delivery.

Embodiment 26: The catheter device of Embodiment 25, where the shaft electrode has a compressible geometry.

Embodiment 27: A catheter device with a shaft and a lumen for passage of a needle device, where the distal portion of the needle has a helical geometry and comprises an exposed electrical conductor for the passage of an electrical current to tissue upon high voltage application for pulsed field ablation delivery, where the helix diameter of the helical geometry is larger when the distal portion of the needle is freely extended outside the lumen of the catheter device than the helix diameter of the helical geometry when the distal portion of the needle is inside the lumen of the catheter device, and where the length of the needle proximal to the distal portion is electrically insulated, with the insulation capable of withstanding a voltage of at least 500 Volts without dielectric breakdown.

Embodiment 28: The catheter device of Embodiment 27, with the distal portion of the shaft of the catheter including at least one shaft electrode that has an electrical polarity opposite to that of the needle during pulsed field ablation delivery.

Embodiment 29: The catheter device of Embodiment 28, where the shaft electrode has a compressible geometry.

Embodiment 30: A catheter device with a shaft and a lumen for passage of a needle device, wherein the distal portion of the needle has a helical geometry and comprises an exposed electrical conductor for the passage of an electrical current to tissue upon high voltage application for pulsed field ablation delivery, wherein the helix diameter of the helical geometry is larger when the distal portion of the needle is freely extended outside the lumen of the catheter device than the helix diameter of the helical geometry when the distal portion of the needle is inside the lumen of the catheter device, wherein the length of the needle proximal to the distal portion is electrically insulated, with the insulation capable of withstanding a voltage of at least 500 Volts without dielectric breakdown, and where a clasping device is attached to the proximal portions of both the catheter shaft and the needle device for clasping the catheter and the needle device so as to provide a means of making controlled movements of the needle device relative to the catheter device.

Embodiment 31: The catheter device of Embodiment 30, where the controlled movement of the needle device comprises a helical motion with the helix pitch equal to that of the helix pitch of the distal portion of the needle when it is freely extended.

Embodiment 32: A method of delivering high voltage pulsed field ablation therapy to tissue, comprising the positioning of a catheter device at an anatomical region of interest, passing a needle device with the distal portion of the needle comprising an exposed electrical conductor through a lumen of the catheter device to puncture a tissue of interest, moving the needle device within the tissue of interest to position its distal tip at a target location, and applying high voltage pulses to the needle device to deliver pulsed field ablation therapy.

Embodiment 33: A method of delivering high voltage pulsed field ablation therapy to tissue, comprising the positioning of a catheter device at an anatomical region of interest, passing a needle device with the distal portion of the needle having a helical geometry and comprising an exposed electrical conductor through a lumen of the catheter device to puncture a tissue of interest, moving the needle device within the tissue of interest to position its distal tip at a target location, and applying high voltage pulses to the needle device to deliver pulsed field ablation therapy, where moving the needle within the tissue comprises a helical motion.

Embodiment 34: The method of Embodiment 33, where the helical motion is driven by operating a clasping device attached to the proximal portions of both the catheter device and the needle.

Embodiment 35: The method of Embodiment 33, where the catheter device is positioned at an anatomical region of interest by passage through a channel of an endoscopic device.

While specific examples have been provided in the figure for exemplary and illustrative purposes, it should be clear that variants such as different numbers of lumens, straight or helical needles or combinations thereof are included in the present disclosure. The needles of the catheter device generally can be attached or connected to an electrical conductor that attaches to a cable or connector cable for delivery of electrical energy from an appropriate generator that can deliver high voltage pulsed field ablation waveforms. Generally, such energy delivery is performed in either unipolar or bipolar mode. In unipolar mode, a subset of the needles has one electrical polarity, while a reference patch placed on the subject has the opposite electrical polarity. In bipolar mode, two different subsets of needles are energized with opposite electrical polarities. In embodiments, multiple paired subsets of needle can be energized in sequential fashion for energy delivery. The pulsed field ablation waveform can be either monophasic (every pulse delivered to an electrode pair has the same polarity) or biphasic in structure (consecutive pulses delivered to an electrode pair have opposite polarities). When the pulsed field ablation waveform is applied, the spatial distribution of the resulting electric field determines the zone of ablation or cell death.

In use of a catheter device of the present invention, various types of image guidance, for example, ultrasound, optical or CT image guidance can be used for visualizing the catheter and confirming target access during positioning. After pulsed field ablation delivery at a target site, the needles can be retracted, the device moved to a different location and the needles inserted again followed by pulsed field ablation delivery at a second target site. The process can continue until a desired volume of tissue or tumor has been treated. In embodiments, more than one ablation can be delivered at a given target site for potential enhancement of the ablation effect.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The invention claimed is:

1. An apparatus, comprising:
   a shaft defining a lumen;
   a shaft electrode having a compressible geometry disposed around a distal portion of the shaft, the shaft electrode configured to transition between an unstressed state in which the shaft electrode has a first outer diameter greater than a diameter of the shaft and a stressed state in which the shaft electrode has a second diameter smaller than the first diameter; and a needle device disposed in the lumen, the needle device having a distal portion that includes an exposed electrical conductor and a proximal portion that is electrically insulated with insulation configured to withstand a voltage of at least about 500 Volts without dielectric breakdown, the distal portion of the needle device having a substantially straight geometry and configured to be inserted into target tissue, the shaft electrode and the needle device being configured to receive a pulsed voltage waveform and to deliver a pulsed electric field via the shaft electrode and the exposed electrical conductor to irreversibly electroporate the target tissue.

2. The apparatus of claim 1, wherein the shaft electrode and the needle device are configured to have opposite polarities during delivery of the pulsed electric field.

3. The apparatus of claim 2, wherein the exposed electrical conductor of the needle device is disposed beyond a distal end of the shaft by between about 3 mm and about 50 mm.

4. The apparatus of claim 1, wherein the first diameter of the shaft electrode in the unstressed state is between about 0.6 mm and about 10 mm.

5. The apparatus of claim 1, wherein the shaft electrode is a first shaft electrode, and the apparatus further comprises:

a second shaft electrode disposed on the distal portion of the shaft.

6. The apparatus of claim 1, wherein the needle device is configured to operate in a unipolar mode to deliver the pulsed electric field.

7. The apparatus of claim 1, wherein the shaft is configured to be positioned through a working channel of an endoscope to an anatomical region of interest.

8. The apparatus of claim 1, wherein the needle device is a first needle device, and the apparatus further comprises:

a second needle device having a distal portion that includes an exposed electrical conductor.

9. The apparatus of claim 8, wherein the distal portion of the second needle device has a substantially straight geometry.

10. The apparatus of claim 1, wherein the exposed electrical conductor of the needle device has a diameter of between about 0.1 mm and about 2.5 mm.

11. The apparatus of claim 1, wherein the exposed electrical conductor includes a hyper-elastic material.

12. The apparatus of claim 1, further comprising:

a proximal actuation assembly attached to proximal portions of the shaft and the needle device, the proximal actuation assembly configured to control a relative movement of the needle device relative to the shaft.

13. The apparatus of claim 1, wherein the shaft electrode has a cage-like structure.

14. An apparatus, comprising:

a shaft defining a lumen;

a shaft electrode having a compressible geometry disposed around a distal portion of the shaft, the shaft electrode configured to transition between an unstressed state in which the shaft electrode has a first outer diameter greater than a diameter of the shaft and a stressed state in which the shaft electrode has a second diameter smaller than the first diameter; and a needle device disposed in the lumen, the needle device having a distal portion that includes an exposed electrical conductor, the distal portion of the needle device being configured to be extended out of the lumen at a non-zero angle with respect to a longitudinal axis of the shaft and to be inserted into target tissue, the shaft electrode and the needle device being configured to receive a pulsed voltage waveform and to deliver a pulsed electric field via the shaft electrode and the exposed electrical conductor to irreversibly electroporate the target tissue.

15. The apparatus of claim 14, wherein the needle device is configured to operate in a unipolar mode to deliver the pulsed electric field.

16. The apparatus of claim 14, wherein the distal portion of the needle device includes a helical geometry.

17. The apparatus of claim 16, wherein the helical geometry is configured to transition from a constrained state to an unconstrained state when the distal portion of the needle device is extended out of the lumen, wherein the helical geometry in the unconstrained state has a diameter that is larger than a diameter of the helical geometry in the constrained state.

18. The apparatus of claim 14, wherein the shaft is configured to be positioned through a working channel of an endoscope to an anatomical region of interest.

19. The apparatus of claim 14, wherein a distal end of the lumen includes a wedge-like structure configured to cause the needle device to be extended out of the lumen at the non-zero angle.

20. The apparatus of claim 14, wherein the needle device is a first needle device, and the apparatus further comprises:

a second needle device having a distal portion that includes an exposed electrical conductor.

21. The apparatus of claim 20, wherein the second needle device is configured to be extended out of the lumen at a non-zero angle with respect to the longitudinal axis of the shaft.

22. The apparatus of claim 20, wherein the first and second needle devices are configured to be extended out of the lumen angled away from one another.

23. An apparatus, comprising:

a shaft defining a lumen;

a shaft electrode having a compressible geometry disposed around a distal portion of the shaft, the shaft electrode configured to transition between an unstressed state in which the shaft electrode has a first outer diameter greater than a diameter of the shaft and a stressed state in which the shaft electrode has a second diameter smaller than the first diameter; and a needle device disposed in the lumen, the needle device having a distal portion that includes an exposed electrical conductor, the distal portion of the needle device having a helical geometry and being configured to be inserted into target tissue, the shaft electrode and the needle device being configured to receive a pulsed voltage waveform and to deliver a pulsed electric field via the shaft electrode and the exposed electrical conductor to irreversibly electroporate the target tissue.

24. The apparatus of claim 23, wherein the distal portion of the needle device is configured to be extended out of the lumen, and the helical geometry is configured to transition from a constrained state to a unconstrained state when the distal portion of the needle device is extended out of the lumen.

25. The apparatus of claim 24, wherein the helical geometry in the unconstrained state has a diameter between about 0.5 mm and about 10 mm.

26. The apparatus of claim 24, wherein the helical geometry in the unconstrained state has a helix pitch of between about 0.3 mm and about 6 mm.

27. The apparatus of claim 24, wherein the helical geometry in the unconstrained state has a length of between about 3 mm and about 50 mm.

28. The apparatus of claim 23, wherein the shaft electrode and the needle device are configured to have opposite polarities during delivery of the pulsed electric field.

29. The apparatus of claim 23, wherein the needle device is a first needle device, and the apparatus further comprises:

a second needle device having a distal portion that includes an exposed electrical conductor.

* * * * *